(12) United States Patent
Kori et al.

(10) Patent No.: US 10,998,197 B2
(45) Date of Patent: May 4, 2021

(54) POLYMER AND COMPOSITION FOR FORMING ORGANIC FILM, SUBSTRATE FOR MANUFACTURING SEMICONDUCTOR APPARATUS, METHOD FOR FORMING ORGANIC FILM, AND PATTERNING PROCESS

(71) Applicant: SHIN-ETSU CHEMICAL CO., LTD., Tokyo (JP)

(72) Inventors: Daisuke Kori, Joetsu (JP); Tsutomu Ogihara, Joetsu (JP); Takeru Watanabe, Joetsu (JP); Keisuke Niida, Joetsu (JP); Takashi Sawamura, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 185 days.

(21) Appl. No.: 16/050,320

(22) Filed: Jul. 31, 2018

(65) Prior Publication Data
US 2019/0067021 A1 Feb. 28, 2019

(30) Foreign Application Priority Data
Aug. 28, 2017 (JP) .............................. JP2017-163691

(51) Int. Cl.
*H01L 29/08* (2006.01)
*H01L 21/308* (2006.01)
(Continued)

(52) U.S. Cl.
CPC .......... *H01L 21/3081* (2013.01); *C07C 15/54* (2013.01); *C08G 8/08* (2013.01);
(Continued)

(58) Field of Classification Search
CPC .......... H01L 21/3081; H01L 21/02282; H01L 21/31116; H01L 21/31138;
(Continued)

(56) References Cited

U.S. PATENT DOCUMENTS 5,607,773 A * 3/1997 Ahlburn ............ H01L 21/02134
257/E21.26
5,705,232 A * 1/1998 Hwang .................. B05D 1/005
427/512
(Continued)

FOREIGN PATENT DOCUMENTS

| JP | 2002-334869 A | 11/2002 |
| JP | 2005-128509 A | 5/2005 |

(Continued)

*Primary Examiner* — Caleb E Henry
(74) *Attorney, Agent, or Firm* — Oliff PLC

(57) ABSTRACT

The invention provides a composition for forming an organic film, which generates no by-product even under such a film formation condition in an inert gas to prevent substrate corrosion, which is capable of forming an organic film not only excellent in properties of filling and planarizing a pattern formed on a substrate but also favorable for dry etching resistance during substrate processing, and further which causes no fluctuation in film thickness of the film due to thermal decomposition even when a CVD hard mask is formed on the organic film. The composition for forming an organic film includes (A) a polymer having a repeating unit shown by the following general formula (1) and (B) an organic solvent.

(Continued)

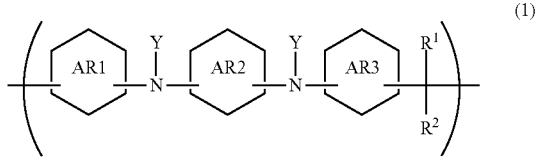

(1)

20 Claims, 2 Drawing Sheets

(51) Int. Cl.
*G03F 7/095* (2006.01)
*G03F 7/09* (2006.01)
*C08L 61/06* (2006.01)
*C07C 15/54* (2006.01)
*C08G 8/08* (2006.01)
*G03F 7/16* (2006.01)
*C09D 161/22* (2006.01)
*H01L 21/033* (2006.01)
*C08L 61/22* (2006.01)
*C08G 16/02* (2006.01)
*H01L 21/02* (2006.01)
*H01L 21/311* (2006.01)

(52) U.S. Cl.
CPC .......... *C08G 16/0231* (2013.01); *C08L 61/06* (2013.01); *C08L 61/22* (2013.01); *C09D 161/22* (2013.01); *G03F 7/094* (2013.01); *G03F 7/095* (2013.01); *G03F 7/168* (2013.01); *H01L 21/0332* (2013.01); *H01L 21/02118* (2013.01); *H01L 21/02282* (2013.01); *H01L 21/31116* (2013.01); *H01L 21/31138* (2013.01)

(58) Field of Classification Search
CPC ........... H01L 21/02118; H01L 21/0273; H01L 21/0332; C09D 161/22; C08L 61/22; C08L 61/06; C08G 16/0231; C08G 8/08; C07C 15/54; G03F 7/168; G03F 7/0035; G03F 7/004; G03F 7/09; G03F 7/095; G03F 7/094
USPC .......................................................... 438/738
See application file for complete search history.

(56) References Cited

U.S. PATENT DOCUMENTS

| | | | | |
|---|---|---|---|---|
| 5,804,259 A * | 9/1998 | Robles | ..................... | B05D 1/60 427/577 |
| 5,855,962 A * | 1/1999 | Cote | ..................... | C03C 17/225 427/376.2 |
| 9,676,892 B2 * | 6/2017 | Kim | ..................... | H01L 21/02282 |
| 9,977,330 B2 * | 5/2018 | Tachibana | ......... | H01L 21/31138 |
| 2005/0255712 A1 | 11/2005 | Kato et al. | | |
| 2009/0274978 A1 | 11/2009 | Ohashi et al. | | |
| 2010/0168346 A1 * | 7/2010 | Lee | ..................... | C08G 65/4006 525/534 |
| 2012/0077345 A1 * | 3/2012 | Saito | ..................... | C08G 12/26 438/703 |
| 2013/0184404 A1 | 7/2013 | Hatakeyama et al. | | |
| 2013/0302990 A1 | 11/2013 | Watanabe et al. | | |
| 2013/0310514 A1 | 11/2013 | Minegishi et al. | | |
| 2014/0235059 A1 | 8/2014 | Sakamoto et al. | | |
| 2014/0235060 A1 | 8/2014 | Shinjo et al. | | |
| 2015/0011092 A1 | 1/2015 | Someya et al. | | |
| 2016/0027653 A1 * | 1/2016 | Tachibana | ............... | G03F 7/094 438/703 |
| 2016/0085152 A1 | 3/2016 | Nakafuji et al. | | |
| 2016/0326396 A1 | 11/2016 | Nishimaki et al. | | |
| 2017/0184968 A1 * | 6/2017 | Kori | ..................... | C07C 49/683 |
| 2018/0284614 A1 * | 10/2018 | Satoh | ..................... | G03F 7/091 |
| 2018/0284615 A1 * | 10/2018 | Nagai | ............... | H01L 21/31133 |

FOREIGN PATENT DOCUMENTS

| | | |
|---|---|---|
| JP | 2006-285095 A | 10/2006 |
| JP | 2006-293298 A | 10/2006 |
| JP | 2007-199653 A | 8/2007 |
| JP | 2009-269953 A | 11/2009 |
| JP | 2010-122656 A | 6/2010 |
| JP | 2010-181605 A | 8/2010 |
| JP | 2012-215842 A | 11/2012 |
| JP | 2013-253227 A | 12/2013 |
| JP | 2016-044272 A | 4/2016 |
| JP | 2016-060886 A | 4/2016 |
| WO | 2004/066377 A1 | 8/2004 |
| WO | 2010/147155 A1 | 12/2010 |
| WO | 2013/005797 A1 | 1/2013 |
| WO | 2013/047516 A1 | 4/2013 |
| WO | 2013/115097 A1 | 8/2013 |
| WO | 2014/208324 A1 | 12/2014 |
| WO | 2015/098594 A1 | 7/2015 |
| WO | 2017/094780 A1 | 6/2017 |

* cited by examiner (G)

(H)

(I)

(J)

(K)

POLYMER AND COMPOSITION FOR FORMING ORGANIC FILM, SUBSTRATE FOR MANUFACTURING SEMICONDUCTOR APPARATUS, METHOD FOR FORMING ORGANIC FILM, AND PATTERNING PROCESS

TECHNICAL FIELD

The present invention relates to: a composition for forming an organic film used to prevent corrosion of substrate materials used in a semiconductor apparatus manufacturing process; a method for forming an organic film and patterning processes according to multilayer resist methods, the method and the processes using the composition for forming an organic film; a substrate for manufacturing a semiconductor apparatus, including the organic film formed on the substrate; and a polymer suitably used in the composition for forming an organic film.

BACKGROUND ART

Conventionally, high integration and high processing speed of semiconductor apparatuses have been achieved through the miniaturization of pattern size by shortening the wavelength of light sources in lithography technology using light exposure (photolithography), which is commonly employed technology. To form such a fine circuit pattern on a semiconductor apparatus substrate (substrate to be processed), the following method is generally employed in which the substrate to be processed is processed by dry etching using a patterned photoresist film as an etching mask. In practice, however, there is no dry etching method capable of providing an absolute etching selectivity between the photoresist film and the substrate to be processed. Hence, recently, it has been common to process a substrate by a multilayer resist method. This method is as follows: first, a middle layer film having a different etching selectivity from a photoresist film (hereinafter, resist upper layer film) is placed between the resist upper layer film and a substrate to be processed; a pattern is formed in the resist upper layer film; then, the pattern is transferred to the middle layer film by dry etching using the resist upper layer film pattern as a dry etching mask; further, the pattern is transferred to the substrate to be processed by dry etching using the middle layer film as a dry etching mask.

One of the multilayer resist methods is a 3-layer resist method which can be performed with a typical resist composition used in a monolayer resist method. In this method, a substrate to be processed is coated with an organic underlayer film composition composed of an organic resin-containing composition and then baked to form an organic underlayer film (hereinafter, organic film); the organic film is subsequently coated with a resist middle layer film composition composed of a composition containing a silicon-containing resin, and baked to form a silicon-containing film (hereinafter, silicon middle layer film); thereafter, a typical organic photoresist film (hereinafter, resist upper layer film) is formed on the silicon middle layer film. The resist upper layer film is patterned and then subjected to dry etching with fluorine-based gas plasma, so that the organic resist upper layer film can exhibit a favorable etching selectivity ratio relative to the silicon middle layer film. Thus, the resist upper layer film pattern can be transferred to the silicon middle layer film. This method allows a pattern to be easily transferred to the silicon middle layer film even if a resist upper layer film does not have film thickness sufficient for directly processing the substrate to be processed or if a resist upper layer film does not have sufficient dry etching resistance for processing the substrate to be processed. This is because the silicon middle layer film generally has a film thickness equal to or smaller than the resist upper layer film. Subsequently, using the silicon middle layer film having the transferred pattern as a dry etching mask, the pattern is transferred to the organic underlayer film by dry etching with oxygen- or hydrogen-based gas plasma. Thereby, the pattern can be transferred to the organic underlayer film having dry etching resistance sufficient for substrate processing. Using this organic underlayer film pattern having the transferred pattern can be transferred to the substrate by dry etching with a fluorine-based gas, chlorine-based gas, or the like.

Meanwhile, the miniaturization in the semiconductor apparatus manufacturing process is approaching to the limit inherent in the wavelength of light sources for photolithography. Accordingly, recently, the high integration of semiconductor apparatuses has been examined. As one means for the high integration, semiconductor apparatuses having complicated structures such as multigate structure have been examined, and some of these have been already put into practical use. In forming such structures by multilayer resist methods, it is possible to employ an organic film composition which is capable of filling a fine pattern including hole, trench, and fin formed on a substrate to be processed with a film without space, and capable of filling a step- or pattern-dense region and a pattern-free region with a film and planarizing the regions. The use of such an organic film composition to form an organic underlayer film having a flat surface on a stepped substrate reduces fluctuations in film thicknesses of a silicon middle layer film and a resist upper layer film formed thereon, and can suppress reductions in a focus margin in photolithography and a margin in a subsequent step of processing the substrate to be processed. This makes it possible to manufacture semiconductor apparatuses with high yields. On the other hand, in the monolayer resist method, the upper resist film has to have a large film thickness to fill a stepped or patterned substrate to be processed. As a result, for example, pattern collapse occurs after exposure and development, and the pattern profile deteriorates due to reflection from the substrate at exposure. Consequently, the pattern formation margin at exposure is narrowed, making it difficult to manufacture semiconductor apparatuses with high yields.

Further, as techniques for the high processing speed of next-generation semiconductor apparatuses, for example, the applications of the following materials have also started to be examined: novel materials having high electron mobility using strained silicon, gallium arsenic, and so forth; and high-precision materials such as ultrathin polysilicon controlled in units of angstrom. However, in substrates to be processed to which such novel high-precision materials are applied, the materials may be corroded by oxygen in air under conditions during the flat film formation from an organic underlayer film composition as described above, for example, film formation conditions of air and 300° C. or higher. Hence, such a performance as a high processing speed of a semiconductor apparatus according to the material design cannot be exhibited, and industrially satisfactory yield may not be achieved. For this reason, an organic underlayer film composition capable of forming a film in an inert gas has been desired so as to avoid a decrease in yield due to substrate corrosion by air under such high temperature conditions.

Conventionally, condensed resins using aromatic alcohols and carbonyl compounds such as ketones and aldehydes as condensing agents for a phenol compound or naphthol compound have been known as materials for forming an organic film for multilayer resist methods. Examples of such condensed resins include a fluorene bisphenol novolak resin described in Patent Document 1, a bisphenol compound and a novolak resin thereof described in Patent Document 2, a novolak resin of an adamantane phenol compound described in Patent Document 3, a bisnaphthol compound and a novolak resin thereof described in Patent Document 4, and the like. Crosslinking by a methylol compound as a crosslinking agent, or a curing action by a crosslinking reaction by oxidation at the α-position of an aromatic ring by the action of oxygen in air and the following condensation causes these materials to form films having solvent resistance in relation to a coating film composition used in the subsequent step.

Moreover, as examples describing a material in which triple bonds are employed as intermolecular linking groups in a curable resin, known are Patent Documents 5, 6, 7, 8, 9, and so forth. However, these materials are not illustrated actually in an inert gas as a curing condition. In addition, formation of cured films from these materials in an inert gas, fluctuation in film thickness due to thermal decomposition under high temperature conditions, and so forth have not been known.

Further, as examples describing a material containing a nitrogen-containing polymer, known are Patent Documents 10 and 11 using a carbazole resin, Patent Document 12 using novolac having a secondary amino group, Patent Document 13 using diarylamine novolac, Patent Document 14 using a copolymer resin containing a heterocycle, Patent Document 15 using indolocarbazole novolac, and so forth. However, these materials are not exemplified regarding the substituent having a triple bond on a nitrogen atom. In addition, cured film formation in an inert gas, fluctuation in film thickness due to thermal decomposition under high temperature conditions, filling property, planarizing property, and so forth have not been known.

CITATION LIST

Patent Literature

Patent Document 1: Japanese Patent Laid-Open Publication No. 2005-128509
Patent Document 2: Japanese Patent Laid-Open Publication No. 2006-293298
Patent Document 3: Japanese Patent Laid-Open Publication No. 2006-285095
Patent Document 4: Japanese Patent Laid-Open Publication No. 2010-122656
Patent Document 5: Japanese Patent Laid-Open Publication No. 2010-181605
Patent Document 6: International Publication No. WO2014-208324
Patent Document 7: Japanese Patent Laid-Open Publication No. 2012-215842
Patent Document 8: Japanese Patent Laid-Open Publication No. 2016-044272
Patent Document 9: Japanese Patent Laid-Open Publication No. 2016-060886
Patent Document 10: International Publication No. WO2010-147155
Patent Document 11: International Publication No. WO2013-005797
Patent Document 12: International Publication No. WO2015-098594
Patent Document 13: International Publication No. WO2013-047516
Patent Document 14: International Publication No. WO2013-115097
Patent Document 15: International Publication No. WO2017-094780

SUMMARY OF THE INVENTION

Technical Problem

The present invention has been made in view of such problems as described above. An object of the present invention is to provide a composition for forming an organic film, which generates no by-product even under such a film formation condition in an inert gas as to prevent substrate corrosion, which is capable of forming an organic film not only excellent in properties of filling and planarizing a pattern formed on a substrate but also favorable for dry etching resistance during substrate processing, and further which causes no fluctuation in film thickness of the film due to thermal decomposition even when a CVD hard mask is formed on the organic film. Another object is to provide: a method for forming an organic film and patterning processes, the method and the processes using the inventive composition for forming an organic film; a substrate for manufacturing a semiconductor apparatus, including the organic film formed on the substrate; and a polymer suitably used in the composition for forming an organic film.

Solution to Problem

To achieve the above object, the present invention provides a composition for forming an organic film, comprising:
(A) a polymer having a repeating unit shown by the following general formula (1); and
(B) an organic solvent,

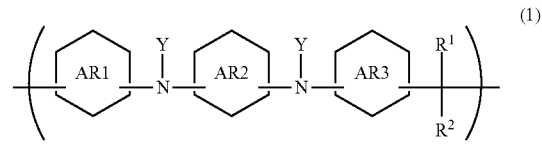

wherein AR1, AR2, and AR3 each represent a benzene ring, a naphthalene ring, or an anthracene ring which optionally have a substituent; carbon atoms on aromatic rings of AR1 and AR2, or AR2 and AR3, optionally bond to each other directly or via a linking group to form a bridge structure; $R^1$ and $R^2$ each independently represent a hydrogen atom or an organic group having 1 to 30 carbon atoms; when $R^1$ and $R^2$ are the organic groups, $R^1$ and $R^2$ optionally bond to each other within a molecule to form a cyclic organic group; and Y represents a group shown by the following formula (2), $$—R^3—C≡C—R^4 \qquad (2)$$

wherein $R^3$ represents a single bond or a divalent organic group having 1 to 20 carbon atoms; $R^4$ represents a hydrogen atom or a monovalent organic group having 1 to 20 carbon atoms; and a dotted line represents a bonding arm.

With the inventive composition for forming an organic film, even when a curing reaction is to be carried out in an oxygen-free inert gas to prevent substrate corrosion due to oxygen in air, the curing reaction can be achieved. The inventive composition is capable of exhibiting a curing performance equivalent to those of conventional underlayer film compositions.

The component (A) preferably has a weight average molecular weight of 500 to 20,000.

The inventive composition for forming an organic film comprising the component (A) having such a weight average molecular weight makes it possible to planarize a more complicated step profile formed on a substrate to be processed.

The composition for forming an organic film preferably further comprises at least one of (C) an acid generator, (D) a surfactant, (E) a crosslinking agent, and (F) a plasticizer.

Incorporating at least one of the components (C) to (F) into the composition for forming an organic film in this manner makes the composition for forming an organic film more excellent in curability, coating property, or planarizing and filling properties.

Moreover, the present invention provides a substrate for manufacturing a semiconductor apparatus, comprising an organic film on the substrate, the organic film being formed by curing the composition for forming an organic film.

In such a substrate for manufacturing a semiconductor apparatus comprising an organic film formed by curing the inventive composition for forming an organic film, the organic film has high dry etching resistance, and also has high filling and planarizing properties. Accordingly, the substrate for manufacturing a semiconductor apparatus does not have fine pores due to insufficient filling or asperity in the organic film surface due to insufficient planarizing property. In addition, the process margin at patterning is increased, making it possible to manufacture semiconductor apparatuses with high yields.

Further, the present invention provides a method for forming an organic film employed in a semiconductor apparatus manufacturing process, the method comprising:

spin-coating a body to be processed with the composition for forming an organic film; and heating the body to be processed coated with the composition for forming an organic film under an inert gas atmosphere at a temperature of 50° C. or higher to 600° C. or lower within a range of 5 seconds to 7200 seconds to obtain a cured film.

Furthermore, the present invention provides a method for forming an organic film employed in a semiconductor apparatus manufacturing process, the method comprising:

spin-coating a body to be processed with the composition for forming an organic film;

heating the body to be processed coated with the composition for forming an organic film in air at a temperature of 50° C. or higher to 300° C. or lower within a range of 5 seconds to 600 seconds to form a coating film; and then heating the body to be processed having the formed coating film under an inert gas atmosphere at a temperature of 200° C. or higher to 600° C. or lower within a range of 10 seconds to 7200 seconds to obtain a cured film.

The inert gas preferably has an oxygen concentration of 1% or less.

The body to be processed preferably has a structure or a step with a height of 30 nm or more.

Setting these conditions as film formation conditions for the inventive composition for forming an organic film reliably suppresses corrosion of a substrate to be processed, making it possible to fill steps on the substrate to be processed into a flatter state.

Moreover, the present invention provides a patterning process comprising:

forming an organic film on a body to be processed from the above-described composition for forming an organic film;

forming a silicon-containing resist middle layer film on the organic film from a silicon-containing resist middle layer film composition;

forming a resist upper layer film on the silicon-containing resist middle layer film from a resist upper layer film composition composed of a photoresist composition;

forming a circuit pattern in the resist upper layer film;

transferring the pattern to the silicon-containing resist middle layer film by etching using the resist upper layer film having the formed circuit pattern as a mask;

transferring the pattern to the organic film by etching using the silicon-containing resist middle layer film having the transferred pattern as a mask; and further transferring the pattern to the body to be processed by etching using the organic film having the transferred pattern as a mask.

Further, the present invention provides a patterning process comprising:

forming an organic film on a body to be processed from the above-described composition for forming an organic film;

forming a silicon-containing resist middle layer film on the organic film from a silicon-containing resist middle layer film composition;

forming an organic antireflective film on the silicon-containing resist middle layer film;

forming a resist upper layer film on the organic antireflective film from a resist upper layer film composition composed of a photoresist composition, so that a 4-layered film structure is constructed;

forming a circuit pattern in the resist upper layer film;

transferring the pattern to the organic antireflective film and the silicon-containing resist middle layer film by etching using the resist upper layer film having the formed circuit pattern as a mask;

transferring the pattern to the organic film by etching using the silicon-containing resist middle layer film having the transferred pattern as a mask; and further transferring the pattern to the body to be processed by etching using the organic film having the transferred pattern as a mask.

Furthermore, the present invention provides a patterning process comprising:

forming an organic film on a body to be processed from the above-described composition for forming an organic film;

forming an inorganic hard mask selected from a silicon oxide film, a silicon nitride film, a silicon oxynitride film, a titanium oxide film, and a titanium nitride film on the organic film;

forming a resist upper layer film on the inorganic hard mask from a resist upper layer film composition composed of a photoresist composition;

forming a circuit pattern in the resist upper layer film;

transferring the pattern to the inorganic hard mask by etching using the resist upper layer film having the formed circuit pattern as a mask;

transferring the pattern to the organic film by etching using the inorganic hard mask having the formed pattern as a mask; and further transferring the pattern to the body to be processed by etching using the organic film having the formed pattern as a mask.

Furthermore, the present invention provides a patterning process comprising:

forming an organic film on a body to be processed from the above-described composition for forming an organic film;

forming an inorganic hard mask selected from a silicon oxide film, a silicon nitride film, a silicon oxynitride film, a titanium oxide film, and a titanium nitride film on the organic film;

forming an organic antireflective film on the inorganic hard mask;

forming a resist upper layer film on the organic antireflective film from a resist upper layer film composition composed of a photoresist composition, so that a 4-layered film structure is constructed;

forming a circuit pattern in the resist upper layer film;

transferring the pattern to the organic antireflective film and the inorganic hard mask by etching using the resist upper layer film having the formed circuit pattern as a mask;

transferring the pattern to the organic film by etching using the inorganic hard mask having the formed pattern as a mask; and further transferring the pattern to the body to be processed by etching using the organic film having the formed pattern as a mask.

The inorganic hard mask is preferably formed by a CVD method or an ALD method.

Additionally, the circuit pattern is preferably formed by a lithography using light with a wavelength ranging from 10 nm to 300 nm, a direct drawing by electron beam, a nanoimprinting, or a combination thereof.

In addition, when the circuit pattern is formed, the circuit pattern is preferably developed by alkaline development or development with an organic solvent.

The body to be processed is preferably a semiconductor apparatus substrate or the semiconductor apparatus substrate coated with any of a metal film, a metal carbide film, a metal oxide film, a metal nitride film, a metal oxycarbide film, and a metal oxynitride film.

The metal of the body to be processed is preferably silicon, titanium, tungsten, hafnium, zirconium, chromium, germanium, copper, silver, gold, aluminum, indium, gallium, arsenic, palladium, iron, tantalum, iridium, molybdenum, or an alloy thereof.

In this manner, when a pattern is formed according to various multilayer resist methods using the inventive composition for forming an organic film, it is possible to precisely transfer the pattern in the resist upper layer film to the body to be processed, thereby forming the pattern in the substrate.

Further, the present invention provides a polymer comprising a repeating unit shown by the following general formula (1),

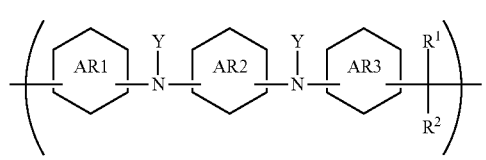 (1)

wherein AR1, AR2, and AR3 each represent a benzene ring, a naphthalene ring, or an anthracene ring which optionally have a substituent; carbon atoms on aromatic rings of AR1 and AR2, or AR2 and AR3, optionally bond to each other directly or via a linking group to form a bridge structure; $R^1$ and $R^2$ each independently represent a hydrogen atom or an organic group having 1 to 30 carbon atoms; when $R^1$ and $R^2$ are the organic groups, $R^1$ and $R^2$ optionally bond to each other within a molecule to form a cyclic organic group; and Y represents a group shown by the following formula (2),

 (2)

wherein $R^3$ represents a single bond or a divalent organic group having 1 to 20 carbon atoms; $R^4$ represents a hydrogen atom or a monovalent organic group having 1 to 20 carbon atoms; and a dotted line represents a bonding arm.

When the inventive polymer is used as a component of a composition for forming an organic film, the obtained composition for forming an organic film is capable of forming an organic film having all of high heat resistance, high dry etching resistance, and high filling and planarizing properties.

Advantageous Effects of Invention

As has been described above, the present invention can provide a polymer useful for forming an organic underlayer film which generates no by-product even under such a film formation condition in an inert gas as to prevent substrate corrosion, and which has both of high filling and planarizing properties; and a composition for forming an organic film, containing this polymer. Moreover, this composition for forming an organic film has excellent filling and planarizing properties without impairing other properties such as heat resistance and etching resistance. Accordingly, the composition for forming an organic film is quite useful as a planarizing material for manufacturing a semiconductor apparatus or a composition for forming an organic film in multilayer resist methods, for example, a 2-layer resist method, a 3-layer resist method using a silicon middle layer film, or a 4-layer resist method using a silicon middle layer film and an organic antireflective film. Further, the inventive methods for forming an organic film make it possible to form a very flat organic film having sufficient organic solvent resistance on a substrate to be processed while suppressing corrosion of the substrate to be processed. Furthermore, the inventive patterning processes make it possible to precisely form a fine pattern in a substrate to be processed according to the multilayer resist methods.

DESCRIPTION OF EMBODIMENTS

Figure 1:
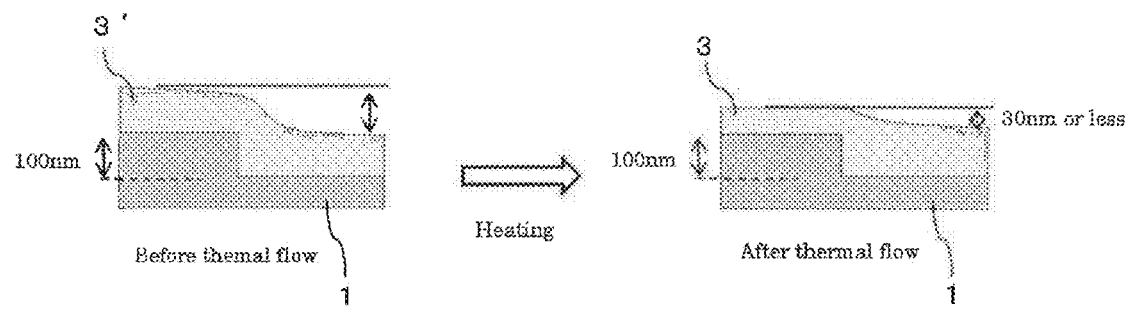
FIG. 1 is an explanatory view of the planarizing property in the present invention.

As described above, it has been desired to develop a composition for forming an organic film, which generates no by-product under such a film formation condition in an inert gas as to prevent substrate corrosion, for example, even at 300° C. or higher, and which is capable of forming an organic underlayer film not only excellent in properties of filling and planarizing a pattern formed on a substrate but also favorable for dry etching resistance during substrate processing. Moreover, it has been desired to develop: a composition for forming an organic film, which causes no fluctuation in film thickness of the organic underlayer film due to thermal decomposition even when a CVD hard mask is formed on the organic underlayer film; a patterning process using the composition for forming an organic film; and a polymer useful in the composition for forming an organic film.

Generally, when an organic underlayer film is formed, a composition is formed by dissolving a compound (polymer) for forming an organic film in an organic solvent. Then, a substrate on which a structure of a semiconductor apparatus, wiring, and so forth have been formed is coated with this composition and baked to form the organic underlayer film. Immediately after the application of the composition, a coating film is formed in a shape according to a step structure on the substrate. Nevertheless, when the coating film is baked, most of the organic solvent is evaporated before curing, so that an organic film is formed from the compound for forming an organic film remaining on the substrate.

In this context, the present inventors have considered that if the compound (polymer) for forming an organic film remaining on the substrate has sufficient thermal flowability, the step profile immediately after the application is planarized by thermal flow, and a flat film can be formed. The present inventors further earnestly studied and consequently found that if a polymer having a repeating unit shown by a general formula (1) is used in a composition for forming an organic film, a substituent shown by Y and having a triple bond provides the composition for forming an organic film with thermosetting property under a film formation condition in an inert gas. Moreover, the composition for forming an organic film generates no by-product during the curing reaction, and the thermal flowability is favorable. Accordingly, the composition for forming an organic film has all of high filling and planarizing properties, favorable dry etching resistance, and such heat resistance that the composition causes no fluctuation in coating film thickness due to thermal decomposition even when a CVD hard mask is formed. These have led to the completion of the present invention.

Specifically, the present invention provides a polymer comprising a repeating unit shown by the following general formula (1),

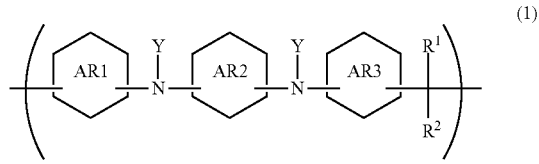

wherein AR1, AR2, and AR3 each represent a benzene ring, a naphthalene ring, or an anthracene ring which optionally have a substituent; carbon atoms on aromatic rings of AR1 and AR2, or AR2 and AR3, optionally bond to each other directly or via a linking group to form a bridge structure; $R^1$ and $R^2$ each independently represent a hydrogen atom or an organic group having 1 to 30 carbon atoms; when $R^1$ and $R^2$ are the organic groups, $R^1$ and $R^2$ optionally bond to each other within a molecule to form a cyclic organic group; and Y represents a group shown by the following formula (2), $$—R^3—C≡C—R^4 \qquad (2)$$

wherein $R^3$ represents a single bond or a divalent organic group having 1 to 20 carbon atoms; $R^4$ represents a hydrogen atom or a monovalent organic group having 1 to 20 carbon atoms; and a dotted line represents a bonding arm.

In addition, the present invention provides a composition for forming an organic film, comprising (A) the aforementioned polymer as a component, and (B) an organic solvent.

Note that, in the present invention, the term planarizing property refers to a performance of planarizing the surface of a substrate. FIG. 1 shows an explanatory view of the planarizing property in the present invention. For example, as shown in FIG. 1, the composition for forming an organic film containing the inventive polymer can reduce a 100-nm step of a substrate 1 to 30 nm or less by coating the substrate 1 with a composition 3' for forming an organic film and heating the resultant to form an organic film 3. Note that the step profile shown in FIG. 1 represents a typical example of the step profile in a substrate for manufacturing a semiconductor apparatus. It is a matter of course that the step profile of a substrate which can be planarized by the composition 3' for forming an organic film containing the inventive polymer is not limited thereto.

Hereinafter, the present invention will be described in detail. However, the present invention is not limited thereto.

<Polymer (Compound for Forming Organic Film)>

The inventive polymer has a repeating unit shown by the following general formula (1).

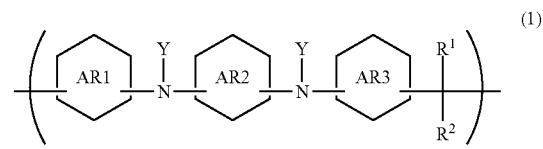

(where AR1, AR2, and AR3 each represent a benzene ring, a naphthalene ring, or an anthracene ring which optionally have a substituent. Carbon atoms on aromatic rings of AR1 and AR2, or AR2 and AR3, may bond to each other directly or via a linking group to form a bridge structure. $R^1$ and $R^2$ each independently represent a hydrogen atom or an organic group having 1 to 30 carbon atoms. When $R^1$ and $R^2$ are organic groups, $R^1$ and $R^2$ may bond to each other within a molecule to form a cyclic organic group. Y represents a group shown by the following formula (2).)

$$—R^3—C≡C—R^4 \qquad (2)$$

(where $R^3$ represents a single bond or a divalent organic group having 1 to 20 carbon atoms. $R^4$ represents a hydrogen atom or a monovalent organic group having 1 to 20 carbon atoms. A dotted line represents a bonding arm.)

Specific examples of the repeating unit shown by (1) include the following. Among the following group, the indenocarbazole type is preferable from the viewpoints of heat resistance and solvent solubility.

-continued
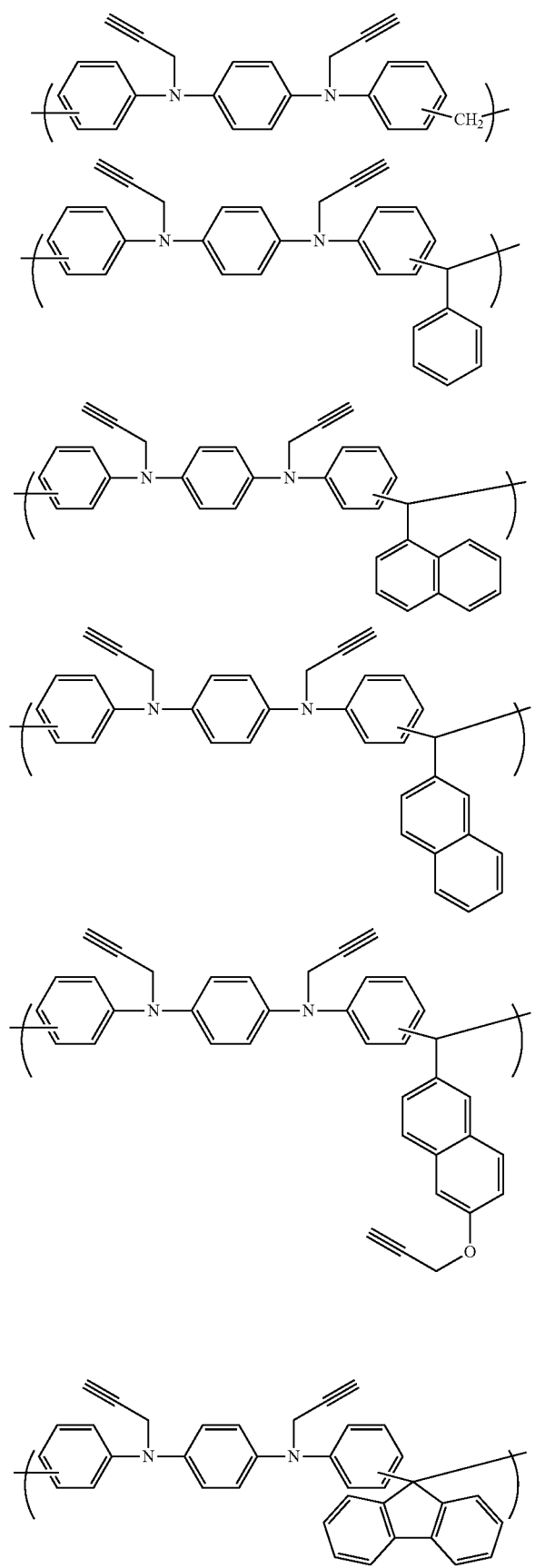
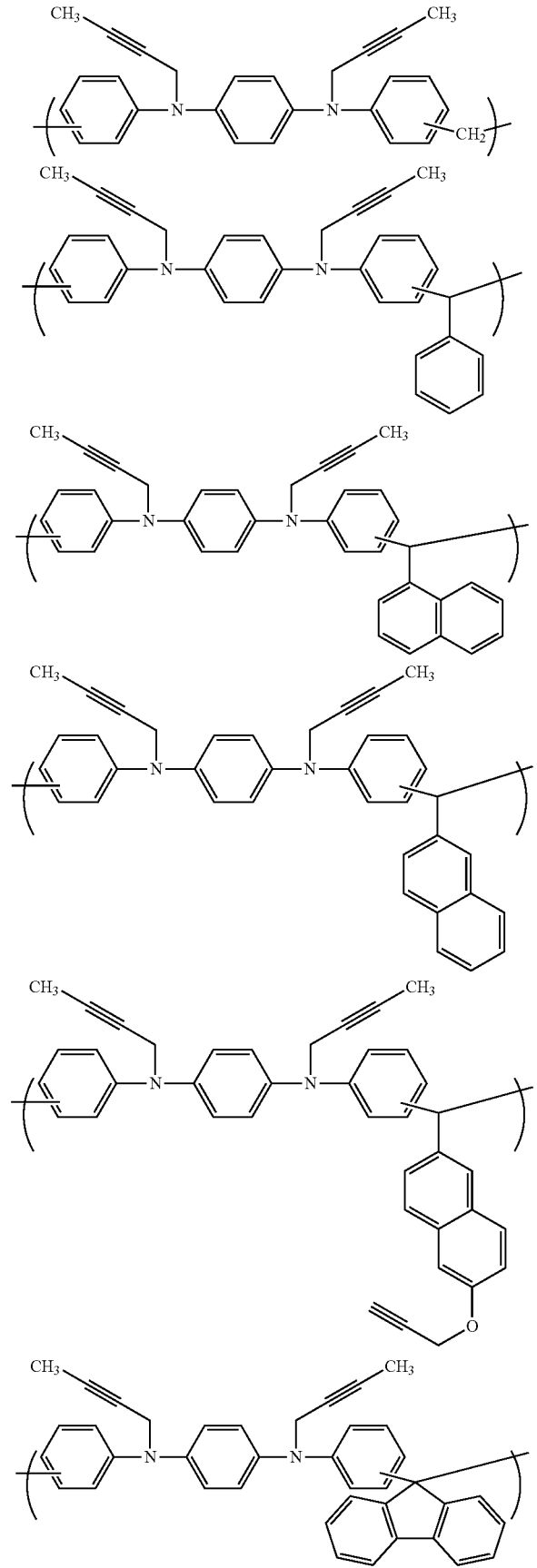

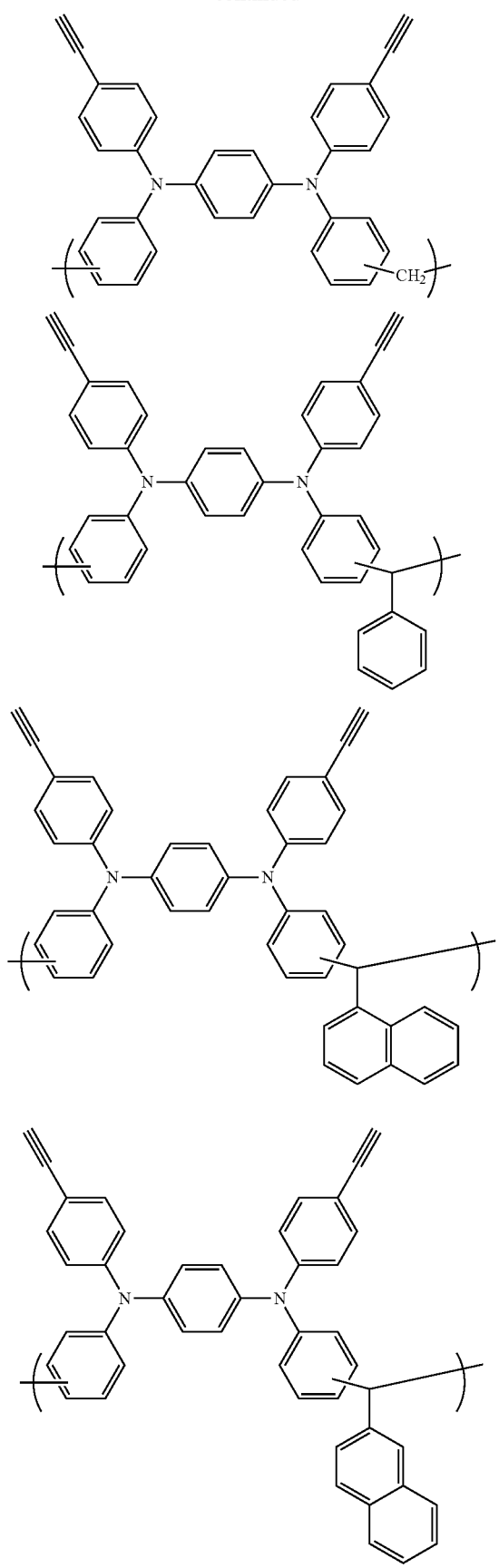
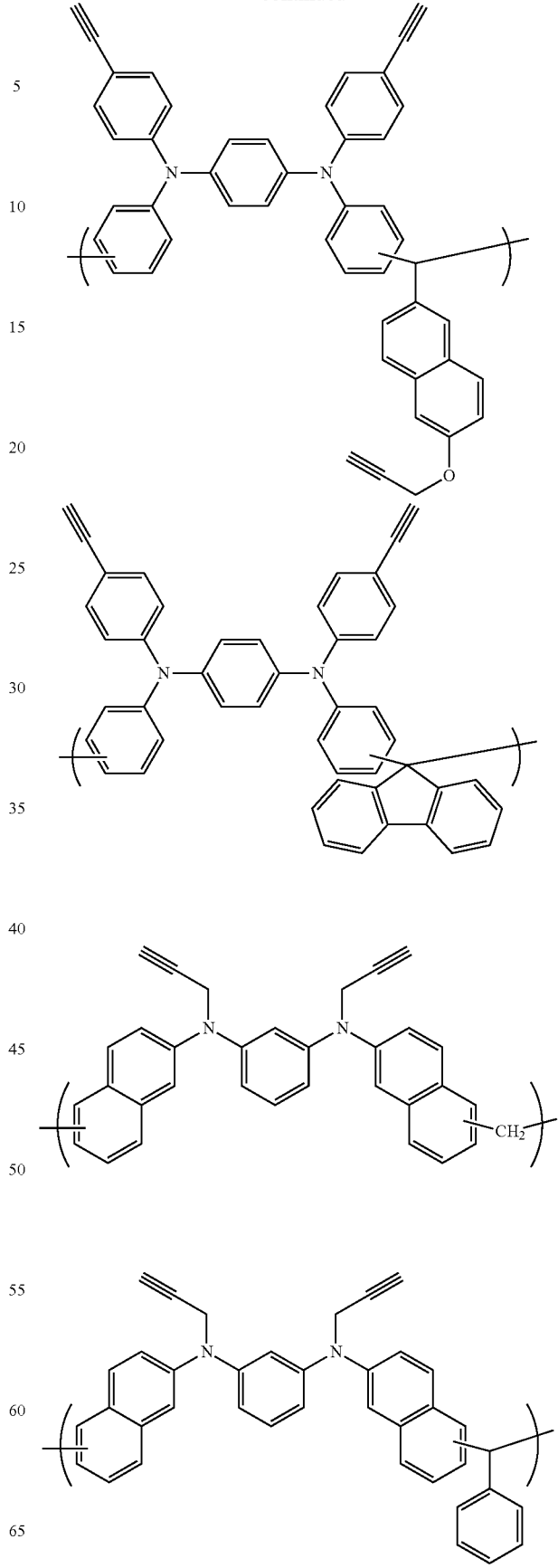

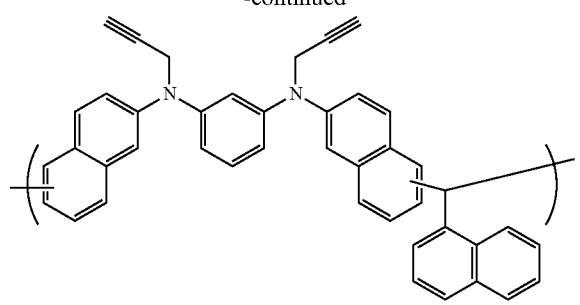
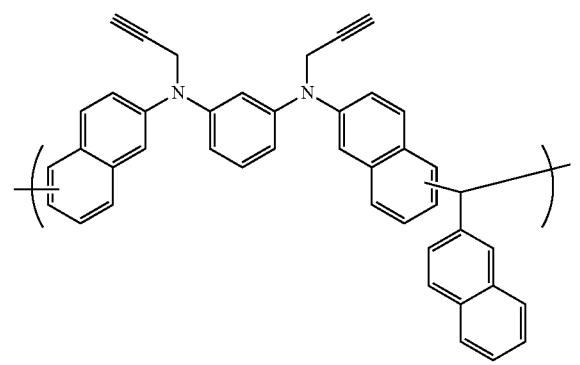
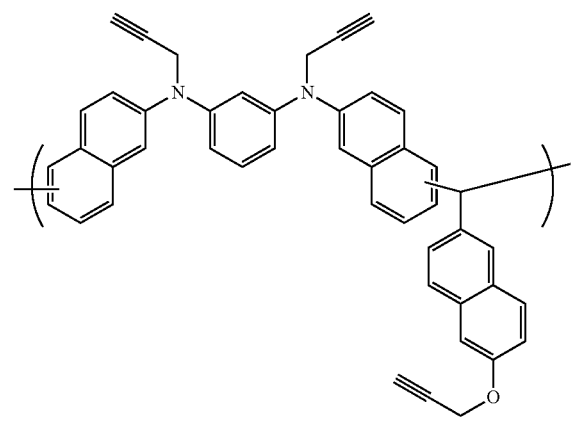
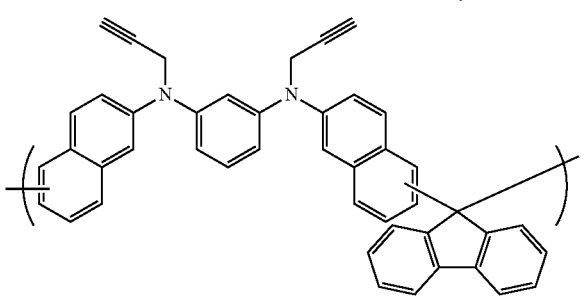
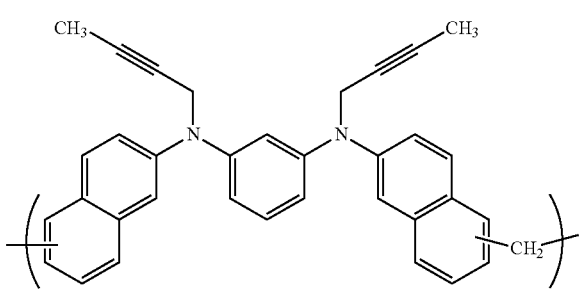
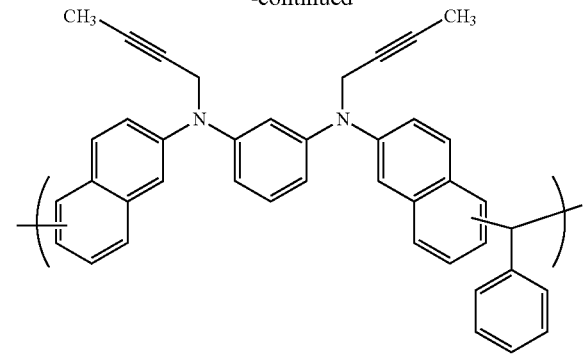
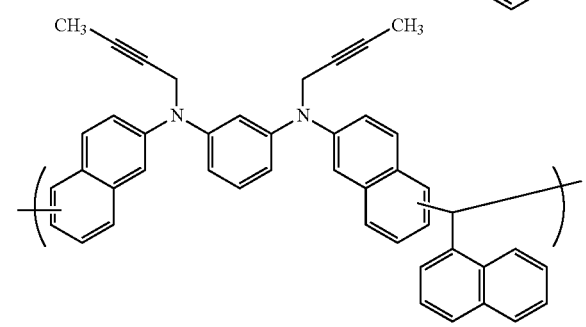
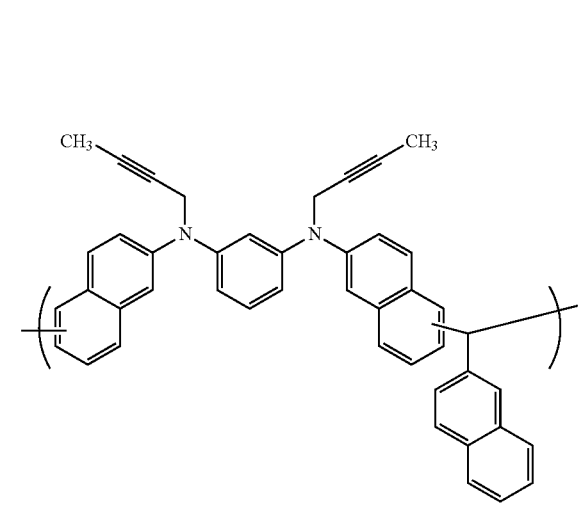
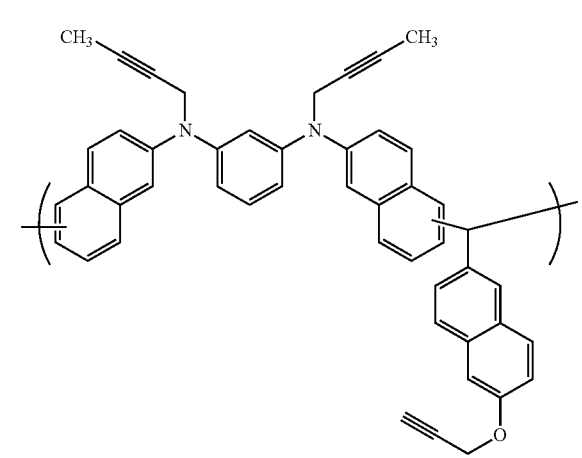

17
-continued
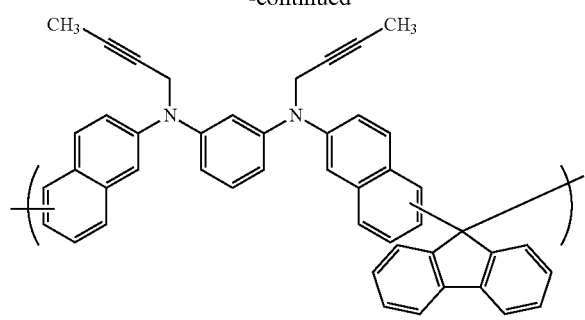
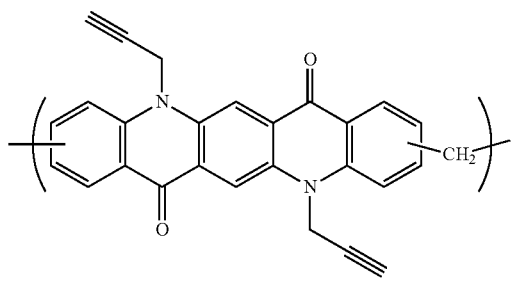
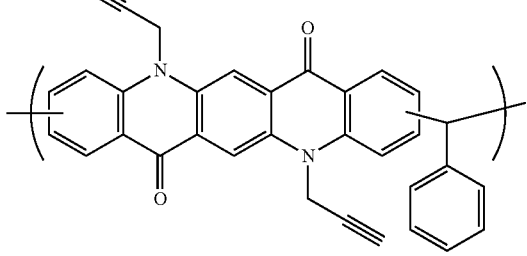
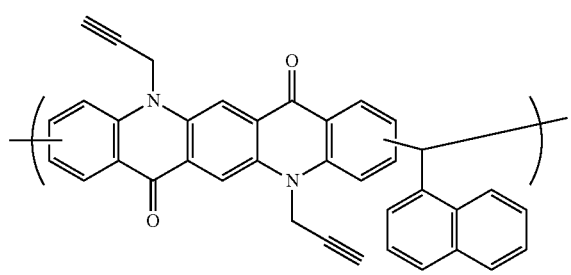
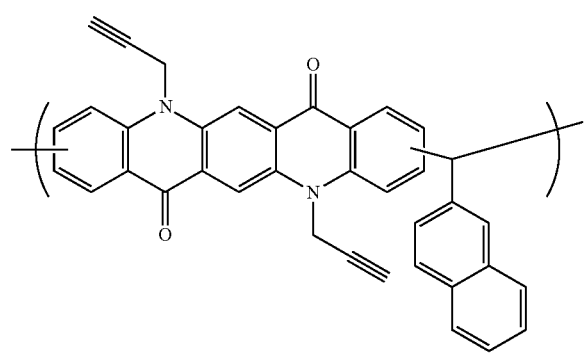
18
-continued
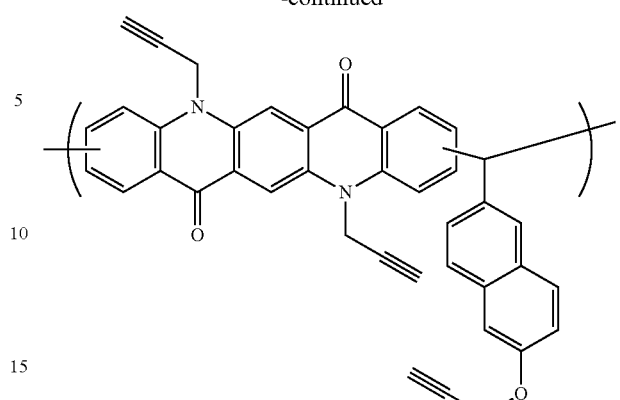
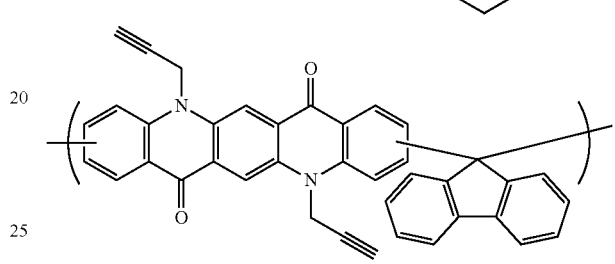
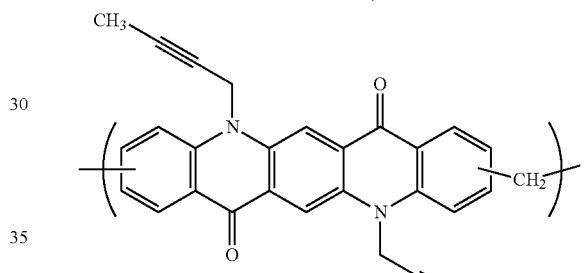
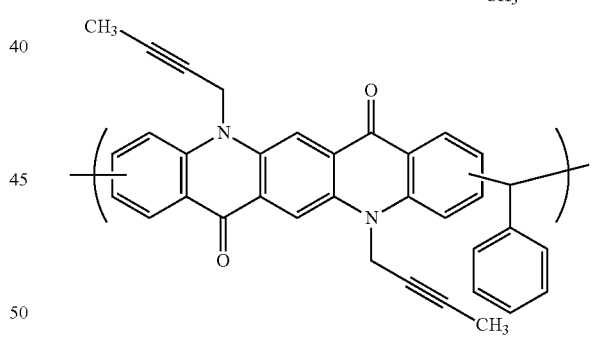
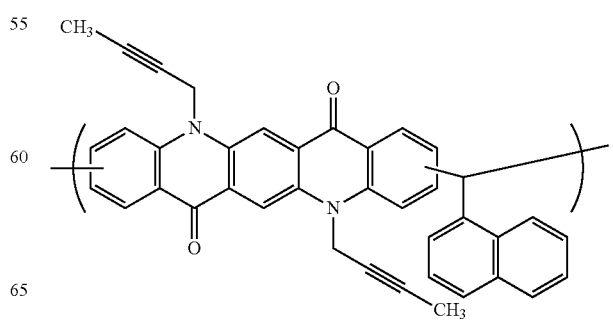

-continued
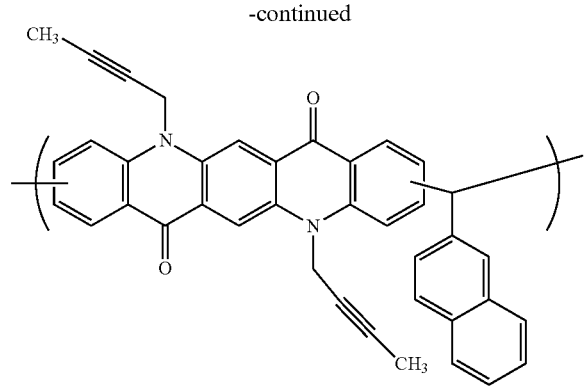
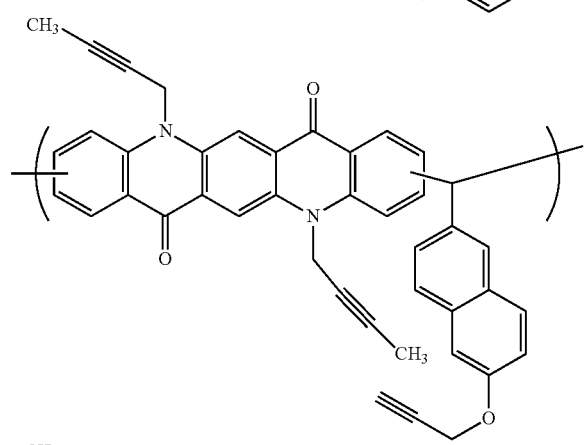
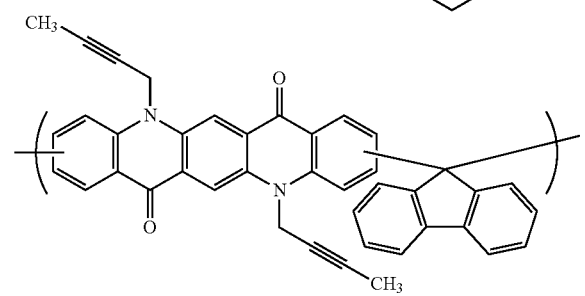
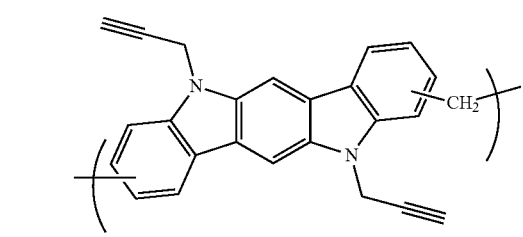
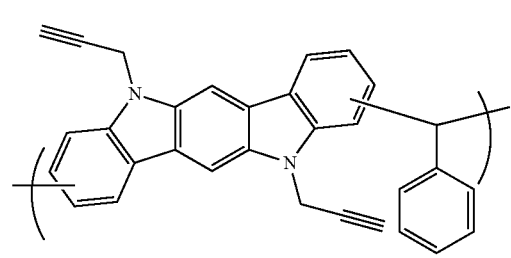
-continued
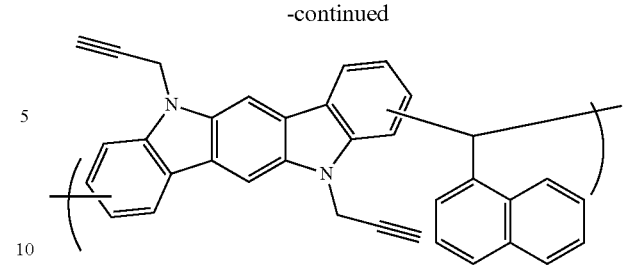
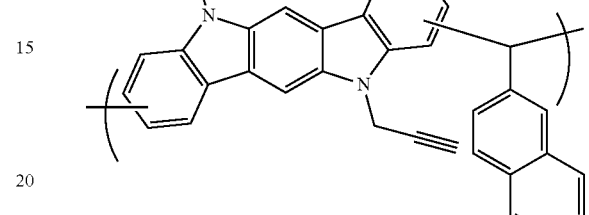
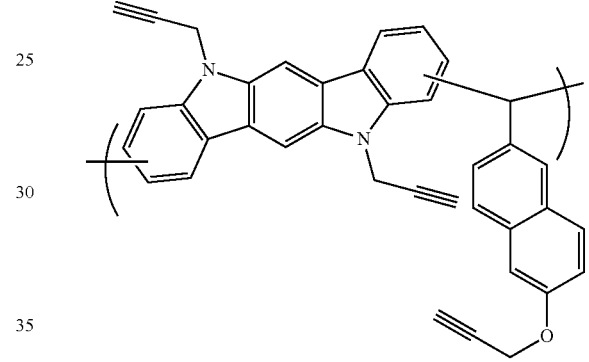
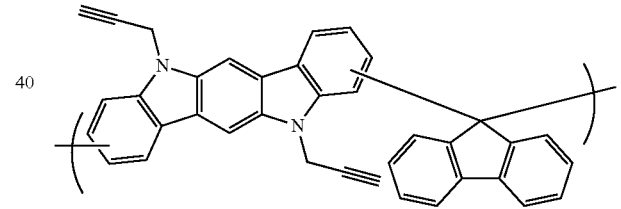
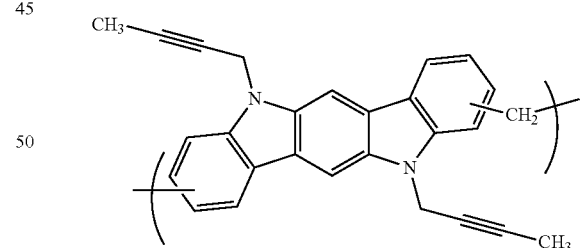
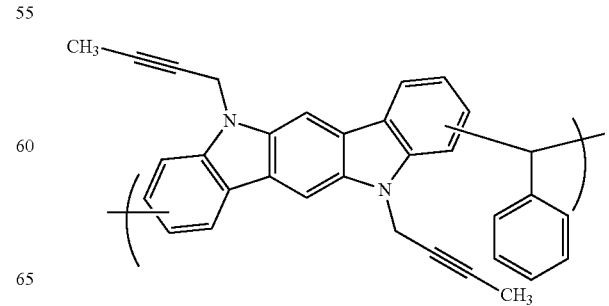

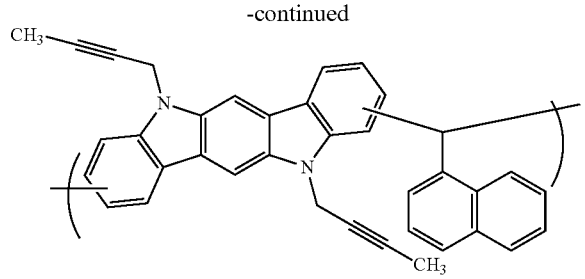
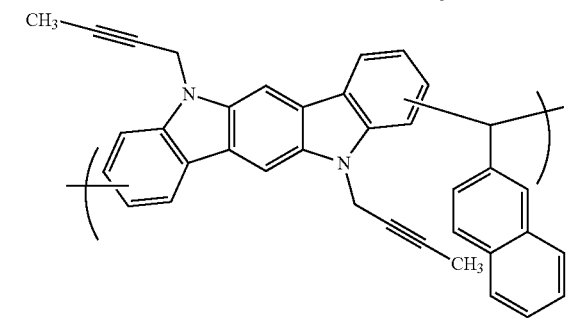
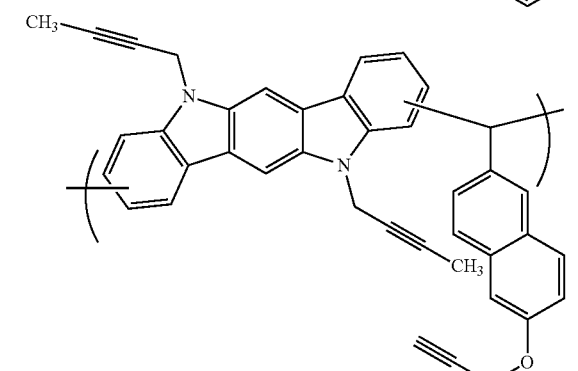
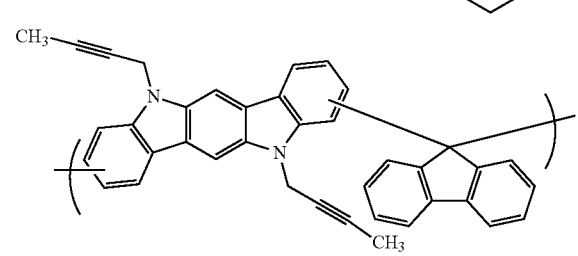
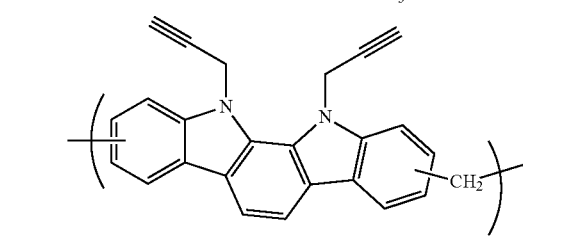
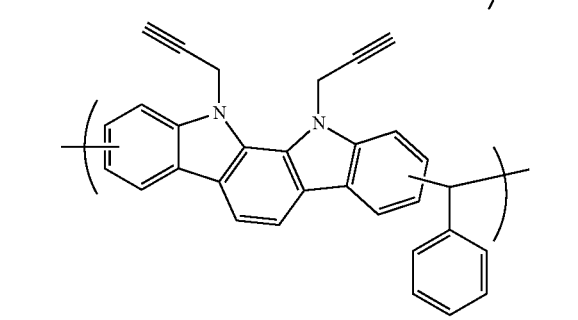
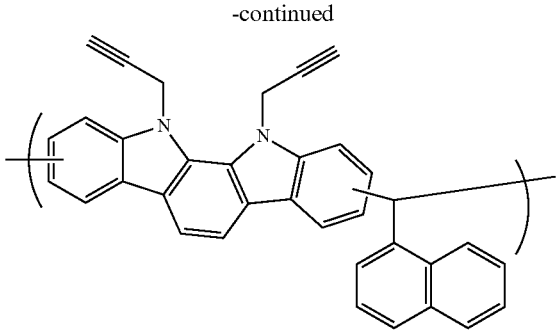
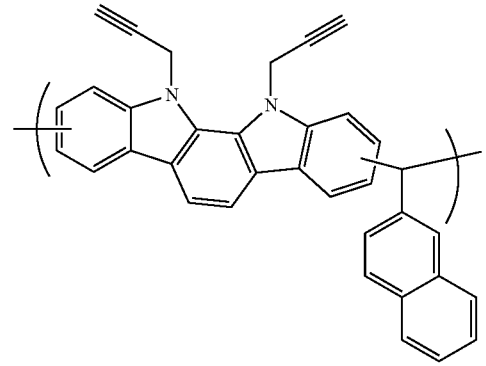
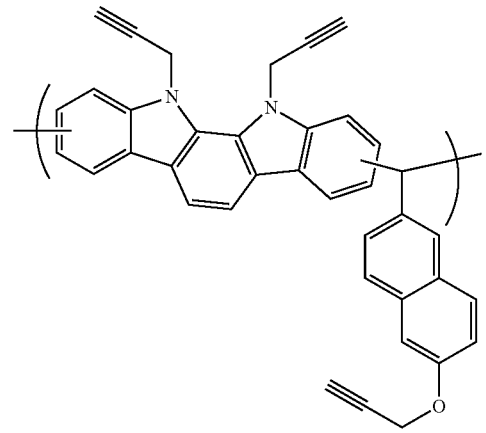
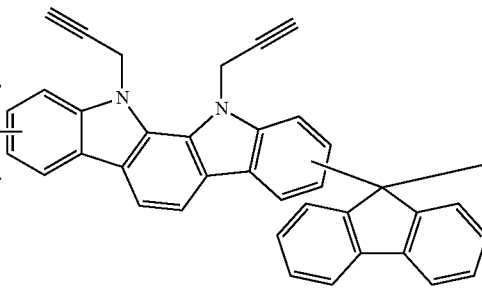
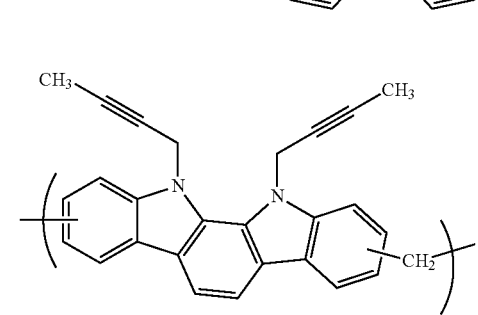

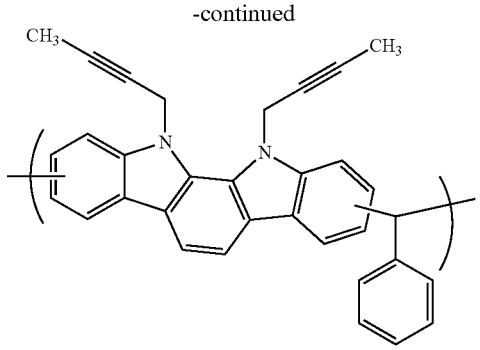
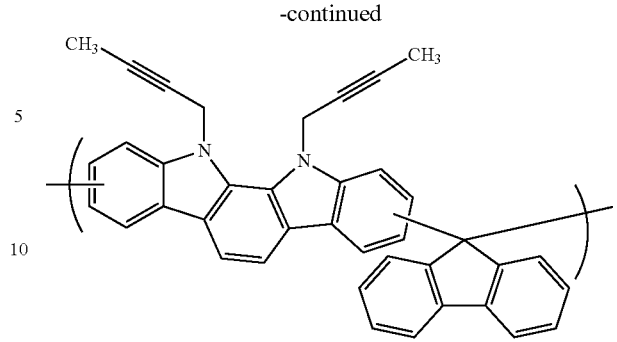
Specific examples of the formula (2) include the following. In the following formulas, * represents a bonding site to a N atom in the formula (1). Among the following group, a propargyl group and a butynyl group are preferable in views of ease of synthesizing the intermediate and availability of the industrial raw material.
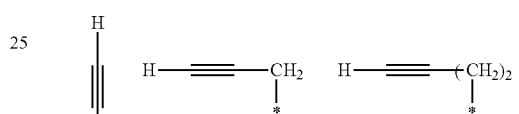
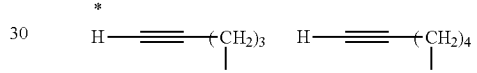
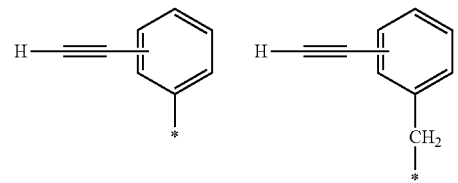
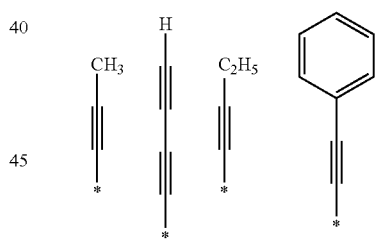
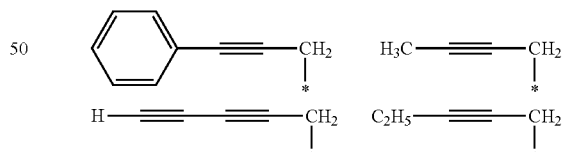
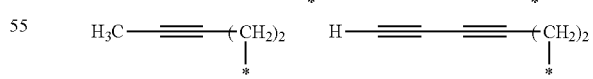
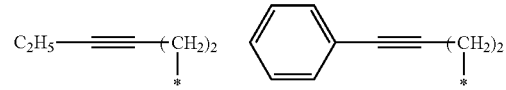
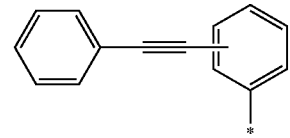

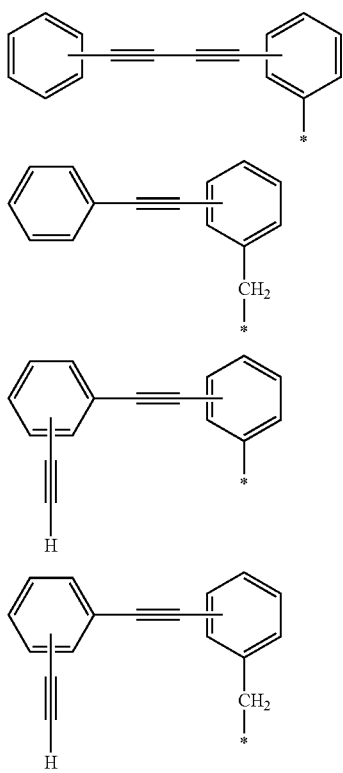
Moreover, the repeating unit of the polymer has a structure shown below as a partial structure.
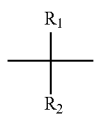
Specific examples of the partial structure include the following. Above all, one having a naphthalene or fluorene structure is preferable from the viewpoints of heat resistance and solvent solubility.
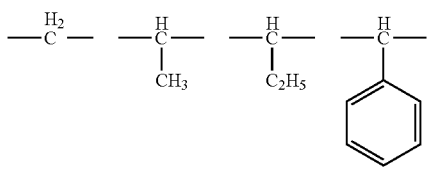
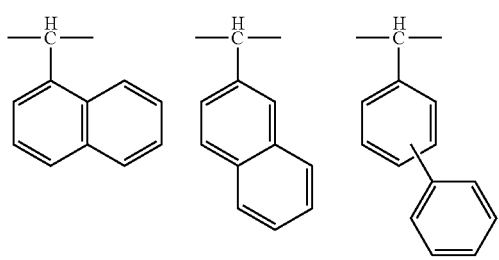
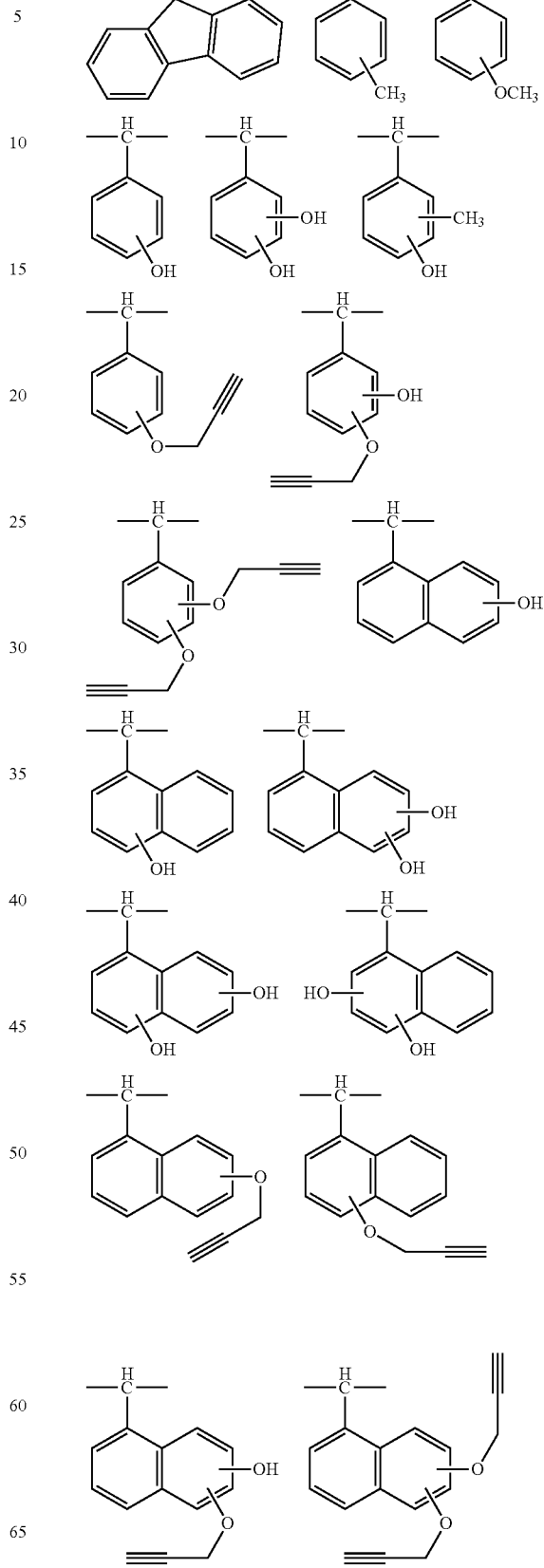

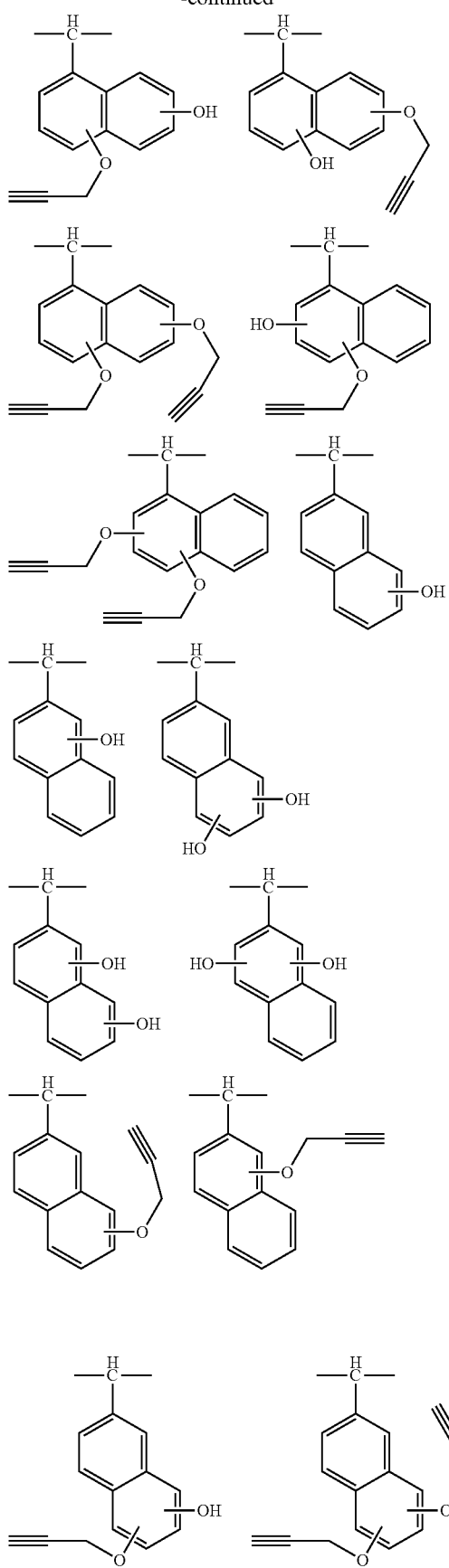
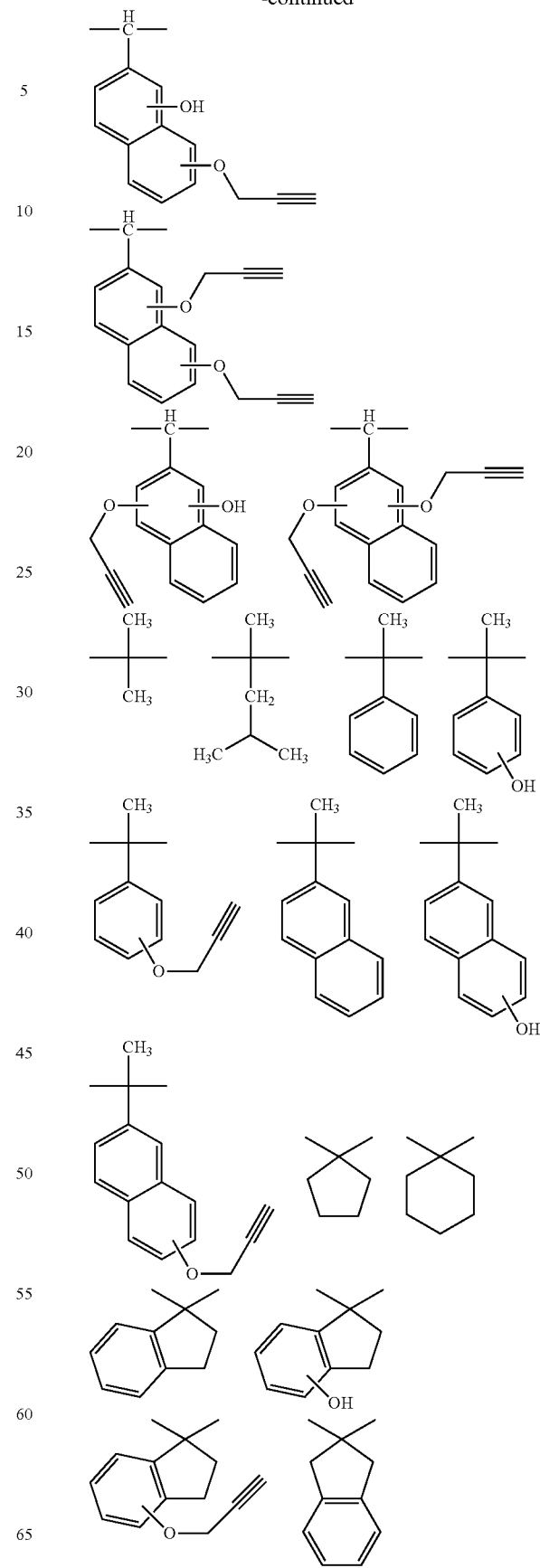

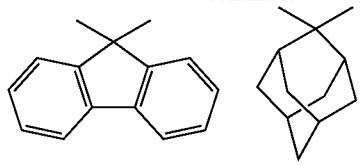

The inventive polymer preferably has a weight average molecular weight of 500 to 20,000 which is calculated based on the general formula (1). From the viewpoints of planarizing property and filling property, the weight average molecular weight is more preferably 15,000 or less. With such a molecular weight, the polymer has more favorable thermal flowability. Accordingly, when blended in a composition for forming an organic film, the polymer can not only favorably fill a fine structure formed on a substrate but also form an organic film having the entire substrate planarized.

[Polymer Production Method]

As means for obtaining the inventive polymer, the inventive polymer can be obtained by a polycondensation reaction between a nitrogen-containing compound and an aldehyde or ketone as shown below. In the following equation, AR1, AR2, AR3, Y, R1, and R2 are as defined above.

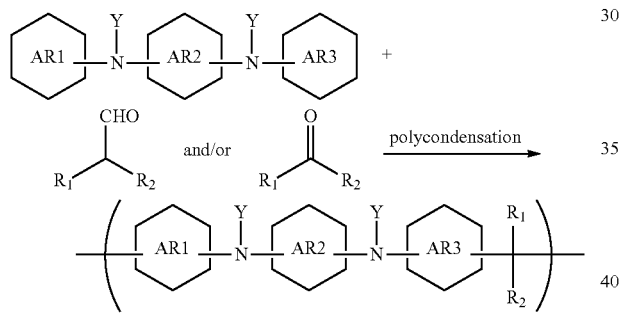

Each of the nitrogen-containing compound, the aldehyde compound, and the ketone compound used in the polycondensation reaction may be used alone, or two or more kinds thereof may be used. It is also possible to use the aldehyde compound and the ketone compound in combination. These can be appropriately selected and combined according to a required property.

Specific examples of the nitrogen-containing compound used in the polycondensation reaction include the following. Above all, an indenocarbazole-based nitrogen-containing compound is preferably used from the viewpoints of heat resistance and solvent solubility of the polymer. In the following formulas, Y is as defined above.

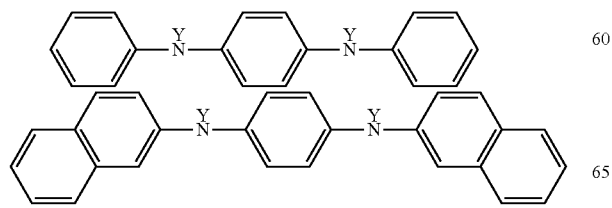

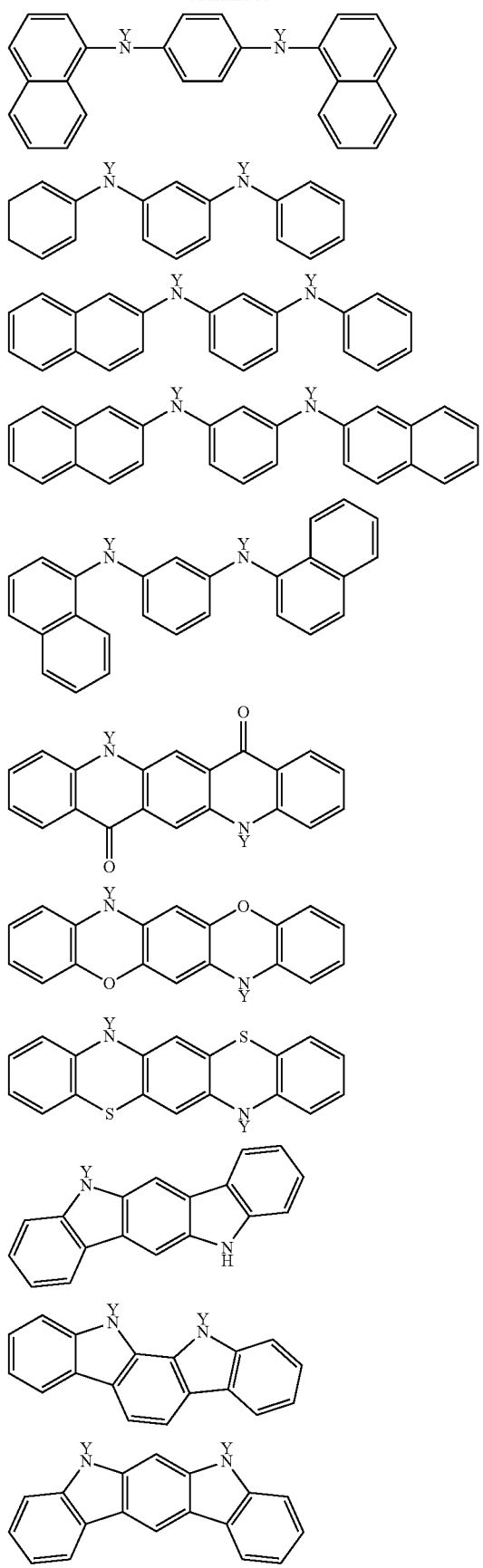

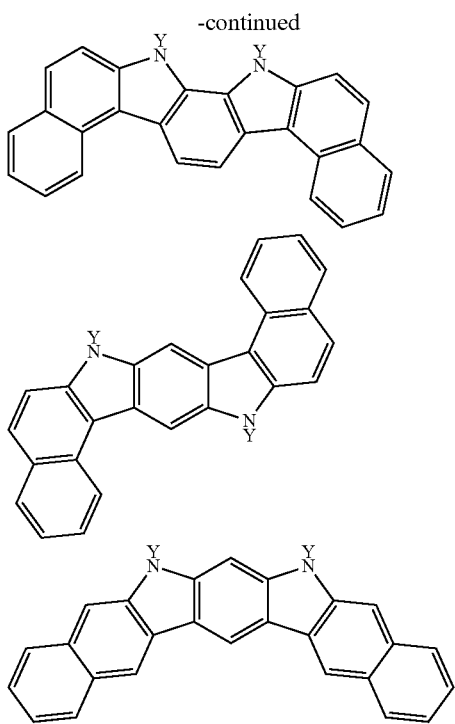

By the polycondensation reaction, the product can be obtained generally in an organic solvent in the presence of an acid catalyst at room temperature or under cooling or heating as necessary. As the acid catalyst used, it is possible to use: inorganic acids such as hydrochloric acid, hydrobromic acid, sulfuric acid, nitric acid, phosphoric acid, and heteropoly acid; organic acids such as oxalic acid, trifluoroacetic acid, methanesulfonic acid, benzenesulfonic acid, p-toluenesulfonic acid, and trifluoromethanesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide.

Examples of the organic solvent used in the polycondensation reaction include alcohols such as methanol, ethanol, isopropyl alcohol, butanol, ethylene glycol, propylene glycol, diethylene glycol, glycerol, ethylene glycol monomethyl ether, and propylene glycol monomethyl ether; ethers such as diethyl ether, dibutyl ether, diethylene glycol diethyl ether, diethylene glycol dimethyl ether, tetrahydrofuran, and 1,4-dioxane; chlorinated solvents such as methylene chloride, chloroform, dichloroethane, and trichloroethylene; hydrocarbons such as hexane, heptane, benzene, toluene, xylene, and cumene; nitriles such as acetonitrile; ketones such as acetone, ethyl methyl ketone, and isobutyl methyl ketone; esters such as ethyl acetate, n-butyl acetate, and propylene glycol methyl ether acetate; non-protic polar solvents such as dimethylsulfoxide, N,N-dimethylformamide, and hexamethylphosphoric triamide; and the like. These can be used alone or in mixture of two or more thereof.

The reaction method includes: a method in which the nitrogen-containing compound, the aldehyde compound or the ketone compound, and acid catalyst are charged at once; a method in which the nitrogen-containing compound and the aldehyde compound or the ketone compound are dispersed or dissolved, and then the acid catalyst is added at once or diluted with a solvent and added dropwise thereto; and a method in which the acid catalyst is dispersed or dissolved, and then the nitrogen-containing compound and the aldehyde compound or the ketone compound are added at once or diluted with a solvent and added dropwise thereto. After completion of the reaction, the resultant may be used directly as the inventive composition for forming an organic film. Alternatively, the resultant may be diluted with an organic solvent, then subjected to liquid separation and washing to remove unreacted raw materials, the acid catalyst, and so on present in the system, and thus collected.

The organic solvent used in the liquid separation and washing is not particularly limited, as long as the organic solvent is capable of dissolving the compounds and being separated into two layers when mixed with water. The organic solvent includes hydrocarbons such as hexane, heptane, benzene, toluene, and xylene; esters such as ethyl acetate, n-butyl acetate, and propylene glycol methyl ether acetate; ketones such as methyl ethyl ketone, methyl amyl ketone, cyclohexanone, and methyl isobutyl ketone; ethers such as diethyl ether, diisopropyl ether, methyl-tert-butyl ether, and ethylcyclopentylmethyl ether; chlorinated solvents such as methylene chloride, chloroform, dichloroethane, and trichloroethylene; mixtures thereof; and the like.

As water used in the liquid separation and washing, generally, what is called deionized water or ultrapure water may be used. The washing may be performed once or more, preferably approximately once to five times because washing ten times or more does not always produce the full washing effects thereof.

In the liquid separation and washing, the washing may be performed with a basic aqueous solution to remove the unreacted raw materials or acidic components in the system. The base contained in the basic aqueous solution specifically includes hydroxides of alkaline metals, carbonates of alkaline metals, hydroxides of alkali earth metals, carbonates of alkali earth metals, ammonia, organic ammonium, and the like.

Further, in the liquid separation and washing, the washing may be performed with an acidic aqueous solution to remove the unreacted raw materials, metal impurities, or basic components in the system. The acid contained in the acidic aqueous solution specifically includes inorganic acids such as hydrochloric acid, hydrobromic acid, sulfuric acid, nitric acid, phosphoric acid, and heteropoly acid; organic acids such as oxalic acid, trifluoroacetic acid, methanesulfonic acid, benzenesulfonic acid, p-toluenesulfonic acid, and trifluoromethanesulfonic acid; and the like.

The liquid separation and washing may be performed with any one of the basic aqueous solution and the acidic aqueous solution, or can be performed with a combination of the two. The liquid separation and washing is preferably performed with the basic aqueous solution and the acidic aqueous solution in this order from the viewpoint of removing the metal impurities.

After the liquid separation and washing with the basic aqueous solution and the acidic aqueous solution, washing with neutral water may be successively performed. The washing may be performed once or more, preferably approximately once to five times. As the neutral water, deionized water, ultrapure water, or the like as mentioned above may be used. The washing may be performed once or more, but if the washing is not performed sufficiently, the basic components and acidic components cannot be removed in some cases. The washing is preferably performed approximately once to five times because washing ten times or more does not always produce the full washing effects thereof.

Further, the reaction product after the liquid separation and washing can also be collected as a powder by concentrating and drying the solvent or crystallizing the reaction product under reduced pressure or normal pressure. Alternatively, the reaction product can also be retained in the state of solution with an appropriate concentration to improve the workability in preparing the composition for forming an organic film. The concentration in this event is preferably 0.1 to 50 mass %, more preferably 0.5 to 30 mass %. With such a concentration, the viscosity is hardly increased, making it possible to prevent deterioration of the workability; in addition, since the amount of the solvent is not excessive, the solution can be prepared economically.

The solvent in this event is not particularly limited, as long as the solvent is capable of dissolving the polymer. Specific examples of the solvent include ketones such as cyclohexanone and methyl-2-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxy propionate, tert-butyl acetate, tert-butyl propionate, and propylene glycol mono-tert-butyl ether acetate. These can be used alone or in mixture of two or more thereof.

To produce the inventive polymer, the nitrogen-containing compound, the aldehyde compound, and the ketone compound can be combined according to a required performance. Compounds containing a side chain structure for improving planarizing property and a rigid aromatic ring structure for improving etching resistance and heat resistance can be combined at a certain ratio. A composition for forming an organic film using the polymer produced using these compounds can achieve both higher filling and planarizing properties as well as higher etching resistance.

[Polymer Production Method (Alternative Method)]

Further, the polymer can also be obtained by a method including: obtaining an intermediate by polycondensation from a nitrogen-containing compound and an aldehyde compound or a ketone compound shown below in the same manner as the above-described polymer production method (Step 1); and then substituting each hydrogen atom on nitrogen with Y (Step 2).

Step 1

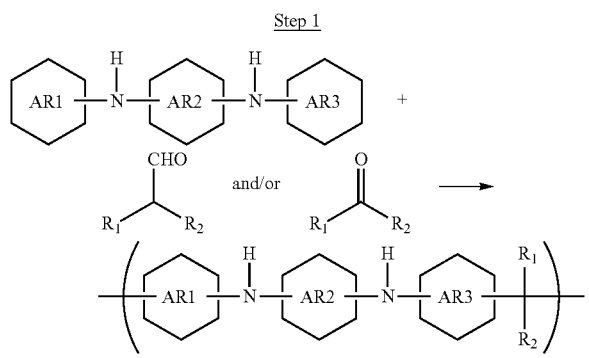

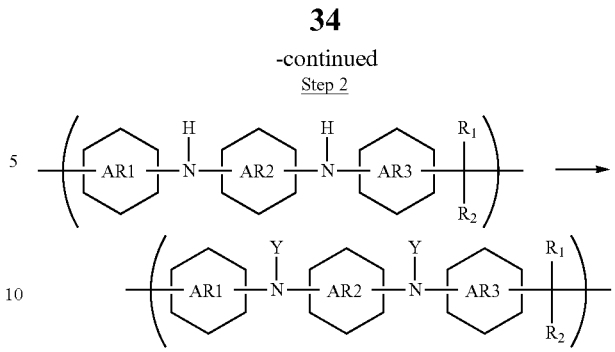

Step 2 is not particularly limited, as long as the reaction enables the introduction of the structure of Y onto each nitrogen atom. As shown in the following equation, examples of the reaction include N-alkylation reaction using a halide, tosylate, or mesylate of Y, and a base catalyst; a coupling reaction using a transition metal catalyst; and the like. In the following equation, X represents a halogen, a tosyl group, or a mesyl group.

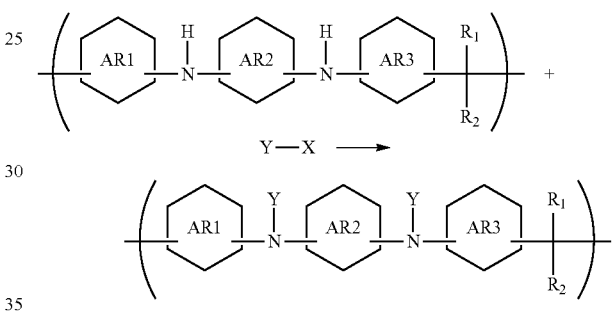

The base catalyst used in the substitution reaction includes inorganic base compounds such as sodium hydrogen carbonate, sodium carbonate, potassium carbonate, calcium carbonate, cesium carbonate, sodium hydroxide, potassium hydroxide, sodium hydride, and potassium phosphate; organic amine compounds such as triethyl amine, pyridine, and N-methylmorpholine; and the like. These can be used alone or in combination of two or more thereof. Meanwhile, in the case where a transition metal catalyst is used, it is possible to use: copper catalysts such as powdered copper, copper chloride, copper bromide, copper iodide, copper acetate, copper hydroxide, and copper nitrate; palladium catalysts such as tris(dibenzylideneacetone)dipalladium and tetrakis(triphenylphosphine)palladium; and the like. These can also be combined with any of the above-described base catalysts.

The solvent used in this alternative method is not particularly limited, as long as the solvent is inactive in the above reaction. Examples of the solvent include ether-based solvents such as diethyl ether, tetrahydrofuran, and dioxane; aromatic solvents such as benzene, toluene, and xylene; acetonitrile, dimethylsulfoxide, N,N-dimethylformamide, N-methylpyrrolidone, water, and the like. These can be used alone or in mixture.

As to the reaction method and the compound collection method, the compound can be collected by the same methods as those in the polymer production method.

Further, in the polymer preparation, two or more kinds of Y—X, or other halide, tosylate, and mesylate than Y—X can be combined according to a required performance. Compounds containing a side chain structure for improving planarizing property and a rigid aromatic ring structure for improving etching resistance and heat resistance can be combined at a certain ratio. A composition for forming an organic film using the polymer produced using these compounds can achieve both higher filling and planarizing properties as well as higher etching resistance.

As described above, when the inventive polymer is used in a composition for forming an organic film, the composition for forming an organic film has favorable dry etching resistance, and also has heat resistance to 400° C. or higher and high filling and planarizing properties.

<Composition for Forming Organic Film>

Further, the present invention provides a composition for forming an organic film, containing the polymer having the repeating unit shown by the general formula (1) as a component (A), and an organic solvent as a component (B).

[(A) Polymer Having Repeating Unit Shown by General Formula (1)]

As the component (A) of the inventive composition for forming an organic film, the same product as the above-described inventive polymer can be used. Note that, as the component (A) in the inventive composition for forming an organic film, the inventive polymer described above can be used alone, or two or more kinds thereof can be used in combination. The component (A) is a base polymer of the inventive composition for forming an organic film.

[(B) Organic Solvent]

The organic solvent usable in the composition for forming an organic film used in the inventive method for forming an organic film is not particularly limited, as long as the organic solvent is capable of dissolving, for example, the component (A), an acid generator, a crosslinking agent, and other additives to be described later. A solvent having a boiling point of lower than 180° C. is preferable. Specifically, the organic solvent includes ketones such as 2-heptanone, cyclopentanone, cyclohexanone, and methyl-2-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxy propionate, tert-butyl acetate, tert-butyl propionate, and propylene glycol mono-tert-butyl ether acetate; and the like. These can be used alone or in mixture of two or more thereof without limitation thereto. Above all, propylene glycol monomethyl ether acetate, propylene glycol monomethyl ether, 2-heptanone, cyclopentanone, cyclohexanone, and a mixture of two or more thereof are preferably used.

The inventive composition for forming an organic film containing the components (A) and (B) can be applied by spin-coating, and has favorable dry etching resistance because the inventive polymer as described above is incorporated. The inventive composition for forming an organic film also has heat resistance to 400° C. or higher and high filling and planarizing properties.

Further, the inventive composition for forming an organic film may use the organic solvent in which a high-boiling-point solvent having a boiling point of 180° C. or higher is added to the aforementioned solvent having a boiling point of lower than 180° C. (a mixture of the solvent having a boiling point of lower than 180° C. with the solvent having a boiling point of 180° C. or higher). The high-boiling-point organic solvent is not particularly limited to hydrocarbons, alcohols, ketones, esters, ethers, chlorinated solvents, and so forth, as long as the high-boiling-point organic solvent is capable of dissolving the polymer. Specific examples of the high-boiling-point organic solvent include 1-octanol, 2-ethylhexanol, 1-nonanol, 1-decanol, 1-undecanol, ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, glycerin, n-nonyl acetate, monohexyl ether, ethylene glycol mono-2-ethylhexyl ether, ethylene glycol monophenyl ether, ethylene glycol monobenzyl ether, diethylene glycol monoethyl ether, diethylene glycol monoisopropyl ether, diethylene glycol mono-n-butyl ether, diethylene glycol monoisobutyl ether, diethylene glycol monohexyl ether, diethylene glycol monophenyl ether, diethylene glycol monobenzyl ether, diethylene glycol diethyl ether, diethylene glycol dibutyl ether, diethylene glycol butylmethyl ether, triethylene glycol dimethyl ether, triethylene glycol monomethyl ether, triethylene glycol-n-butyl ether, triethylene glycol butylmethyl ether, triethylene glycol diacetate, tetraethylene glycol dimethyl ether, dipropylene glycol monomethyl ether, dipropylene glycol mono-n-propyl ether, dipropylene glycol mono-n-butyl ether, tripropylene glycol dimethyl ether, tripropylene glycol monomethyl ether, tripropylene glycol mono-n-propyl ether, tripropylene glycol mono-n-butyl ether, ethylene glycol monoethyl ether acetate, ethylene glycol monobutyl ether acetate, diethylene glycol monomethyl ether acetate, diethylene glycol monoethyl ether acetate, diethylene glycol monobutyl ether acetate, triacetin, propylene glycol diacetate, dipropylene glycol monomethyl ether acetate, dipropylene glycol methyl-n-propyl ether, dipropylene glycol methyl ether acetate, 1,4-butanediol diacetate, 1,3-butylene glycol diacetate, 1,6-hexanediol diacetate, γ-butyrolactone, dihexyl malonate, diethyl succinate, dipropyl succinate, succinate dibutyl, succinate dihexyl, dimethyl adipate, diethyl adipate, dibutyl adipate, and the like. These may be used alone or in mixture of two or more thereof.

The boiling point of the high-boiling-point solvent may be appropriately selected according to the temperature at which the composition for forming an organic film is heated. The boiling point of the high-boiling-point solvent to be added is preferably 180° C. to 300° C., more preferably 200° C. to 300° C. The boiling point of 180° C. or higher prevents the evaporation rate at baking (heating) from becoming excessive, which would otherwise occur if the boiling point is too low. Thus, the boiling point of 180° C. or higher can provide sufficient thermal flowability and is preferable. Meanwhile, when the boiling point is 300° C. or lower, the boiling point is not too high, so that the high-boiling-point solvent evaporates after baking and does not remain in the film; thus, the boiling point of 300° C. or lower does not affect the film physical properties such as etching resistance and is preferable.

When the high-boiling-point solvent is used, the formulation amount of the high-boiling-point solvent is preferably 1 to 30 parts by mass based on 100 parts by mass of the solvent having a boiling point of lower than 180° C. The formulation amount in this range prevents a failure in providing sufficient thermal flowability during baking, which would otherwise occur if the formulation amount is too small. In addition, deterioration of the film physical properties such as etching resistance is prevented, which would otherwise occur if the formulation amount is so large that the solvent remains in the film. Thus, the formulation amount in the above range is preferable.

When the composition for forming an organic film contains such a high-boiling-point solvent, the above-described polymer is provided with thermal flowability by adding the high-boiling-point solvent, so that the composition for forming an organic film also has high filling and planarizing properties.

[(C) Acid Generator]

In the inventive composition for forming an organic film, (C) an acid generator can be added so as to further promote the curing reaction. The acid generator includes a material that generates an acid by thermal decomposition, and a material that generates an acid by light irradiation. Any acid generator can be added. Examples of the component (c) include onium salts, diazomethane derivatives, glyoxime derivatives, bissulfone derivatives, sulfonic acid esters of N-hydroxyimide compounds, R-ketosulfonic acid derivatives, disulfone derivatives, nitrobenzylsulfonate derivatives, sulfonic acid ester derivatives, and the like. Specifically, acid generators disclosed in paragraphs (0061) to (0085) of Japanese Patent Laid-Open Publication No. 2007-199653 can be added, but the present invention is not limited thereto.

The acid generators can be used alone or in combination of two or more thereof. When the acid generator is added, the added amount is preferably 0.05 to 50 parts by mass, more preferably 0.1 to 10 parts by mass, based on 100 parts by mass of the compound (A).

[(D) Surfactant]

To the inventive composition for forming an organic film, (D) a surfactant can be added so as to enhance the coating property in spin coating. Examples of the surfactant include polyoxyethylene alkyl ethers, polyoxyethylene alkylallyl ethers, polyoxyethylene polyoxypropylene block copolymers, sorbitan fatty acid esters, nonionic surfactants, fluorinated surfactants, and the like. Specifically, those disclosed in (0142) to (0147) of Japanese Patent Laid-Open Publication No. 2009-269953 can be used, but the present invention is not limited thereto.

[(E) Crosslinking Agent]

Moreover, to the inventive composition for forming an organic film, (E) a crosslinking agent can also be added so as to increase the curability and to further suppress intermixing with an upper layer film. The crosslinking agent is not particularly limited, and known various types of crosslinking agents can be widely used. Examples thereof include melamine-based crosslinking agents, glycoluril-based crosslinking agents, benzoguanamine-based crosslinking agents, urea-based crosslinking agents, R-hydroxyalkylamide-based crosslinking agents, isocyanurate-based crosslinking agents, aziridine-based crosslinking agents, oxazoline-based crosslinking agents, and epoxy-based crosslinking agents.

Specific examples of the melamine-based crosslinking agents include hexamethoxymethylated melamine, hexabutoxymethylated melamine, alkoxy- and/or hydroxy-substituted derivatives thereof, and partial self-condensates thereof. Specific examples of the glycoluril-based crosslinking agents include tetramethoxymethylated glycoluril, tetrabutoxymethylated glycoluril, alkoxy- and/or hydroxy-substituted derivatives thereof, and partial self-condensates thereof. Specific examples of the benzoguanamine-based crosslinking agents include tetramethoxymethylated benzoguanamine, tetrabutoxymethylated benzoguanamine, alkoxy- and/or hydroxy-substituted derivatives thereof, and partial self-condensates thereof. Specific examples of the urea-based crosslinking agents include dimethoxymethylated dimethoxyethyleneurea, alkoxy- and/or hydroxy-substituted derivatives thereof, and partial self-condensates thereof. A specific example of the β-hydroxyalkylamide-based crosslinking agents includes N,N,N',N'-tetra(2-hydroxyethyl)adipic acid amide. Specific examples of the isocyanurate-based crosslinking agents include triglycidyl isocyanurate and triallyl isocyanurate. Specific examples of the aziridine-based crosslinking agents include 4,4'-bis(ethyleneiminocarbonylamino)diphenylmethane and 2,2-bishydroxymethylbutanol-tris[3-(1-aziridinyl)propionate]. Specific examples of the oxazoline-based crosslinking agents include 2,2'-isopropylidene bis(4-benzyl-2-oxazoline), 2,2'-isopropylidene bis(4-phenyl-2-oxazoline), 2,2'-methylenebis4,5-diphenyl-2-oxazoline, 2,2'-methylenebis-4-phenyl-2-oxazoline, 2,2'-methylenebis-4-tert-butyl-2-oxazoline, 2,2'-bis(2-oxazoline), 1,3-phenylenebis(2-oxazoline), 1,4-phenylenebis(2-oxazoline), and a 2-isopropenyloxazoline copolymer. Specific examples of the epoxy-based crosslinking agents include diglycidyl ether, ethylene glycol diglycidyl ether, 1,4-butanediol diglycidyl ether, 1,4-cyclohexanedimethanol diglycidyl ether, poly(glycidyl methacrylate), trimethylolethane triglycidyl ether, trimethylolpropane triglycidyl ether, and pentaerythritol tetraglycidyl ether.

[(F) Plasticizer]

Further, to the inventive composition for forming an organic film, (F) a plasticizer can be added so as to further enhance the planarizing and filling properties. The plasticizer is not particularly limited, and known various types of plasticizers can be widely used. Examples thereof include low-molecular-weight compounds such as phthalic acid esters, adipic acid esters, phosphoric acid esters, trimellitic acid esters, and citric acid esters; and polymers such as polyethers, polyesters, and polyacetal-based polymers disclosed in Japanese Patent Laid-Open Publication No. 2013-253227.

[(G) Other Additives]

Further, the inventive composition for forming an organic film can be blended, as necessary, with other components than the components (A) to (F) described above.

Particularly, like the plasticizer, as an additive for providing the inventive composition for forming an organic film with filling and planarizing properties, it is preferable to use, for example, liquid additives having polyethylene glycol and polypropylene glycol structures, or thermo-decomposable polymers having a weight loss ratio between 30° C. and 250° C. of 40 mass % or more and a weight average molecular weight of 300 to 200,000. The thermo-decomposable polymers preferably contain a repeating unit having an acetal structure shown by the following general formula (DP1) or (DP1a).

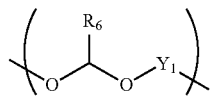

(DP1)

(where $R_6$ represents a hydrogen atom or a saturated or unsaturated monovalent organic group having 1 to 30 carbon atoms which may be substituted. Y1 represents a saturated or unsaturated divalent organic group having 2 to 30 carbon atoms.)

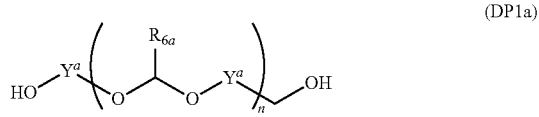

(DP1a)

(where $R_{6a}$ represents an alkyl group having 1 to 4 carbon atoms. $Y^a$ represents a saturated or unsaturated divalent hydrocarbon group having 4 to 10 carbon atoms which may have an ether bond. n represents an average repeating unit number of 3 to 500.)

As described above, the inventive composition for forming an organic film is a composition for forming an organic film having favorable dry etching resistance and also having heat resistance to 400° C. or higher and high filling and planarizing properties. Thus, the inventive composition for forming an organic film is quite useful as a composition for forming an organic film in multilayer resist methods such as a 2-layer resist method, a 3-layer resist method using a silicon-containing resist middle layer film or a silicon-containing inorganic hard mask, and a 4-layer resist method using a silicon-containing resist middle layer film or a silicon-containing inorganic hard mask and an organic anti-reflective film. Moreover, the inventive composition for forming an organic film generates no by-product even during film formation in an inert gas, and has excellent filling and planarizing properties. Accordingly, the inventive composition for forming an organic film can also be suitably used as a planarizing material in a semiconductor apparatus manufacturing process, besides the multilayer resist methods.

<Substrate for Manufacturing Semiconductor Apparatus>

Additionally, the present invention provides a substrate for manufacturing a semiconductor apparatus, including an organic film on the substrate, the organic film being formed by curing the above-described composition for forming an organic film.

<Method for Forming Organic Film>

Moreover, the present invention provides a method for forming an organic film employed in a semiconductor apparatus manufacturing process, the method including:

spin-coating a substrate to be processed with the above-described inventive composition for forming an organic film;

heating the body to be processed coated with the composition for forming an organic film under an inert gas atmosphere at a temperature of 50° C. or higher to 600° C. or lower within a range of 5 seconds to 7200 seconds to obtain a cured film.

Further, the present invention provides a method for forming an organic film employed in a semiconductor apparatus manufacturing process, the method including:

spin-coating a substrate to be processed with the above-described inventive composition for forming an organic film;

heating the body to be processed coated with the composition for forming an organic film in air at a temperature of 50° C. or higher to 300° C. or lower within a range of 5 seconds to 600 seconds to form a coating film; and then heating the body to be processed having the formed coating film under an inert gas atmosphere at a temperature of 200° C. or higher to 600° C. or lower within a range of 10 seconds to 7200 seconds to obtain a cured film.

In these methods for forming an organic film, first, a substrate to be processed is spin-coated with the above-described inventive composition for forming an organic film. By employing the spin coating method, favorable filling property can be obtained. After the spin coating, baking (heating) is performed to promote the planarization attributable to thermal flow and the crosslinking reaction. Note that since this baking allows the solvent in the composition to evaporate, even when a resist upper layer film or a silicon-containing resist middle layer film is formed on the organic film, the mixing can be prevented.

The film formation step by heating to form an organic underlayer film using the inventive composition for forming an organic film can employ 1-stage baking, 2-stage baking, or multi-stage baking of three or more stages. Nevertheless, the 1-stage baking or the 2-stage baking is economically preferable. The film formation by the 1-stage baking is performed at a temperature of 50° C. or higher to 600° C. or lower within a range of 5 to 7200 seconds, preferably at a temperature of 100° C. or higher to 500° C. or lower within a range of 10 to 3600 seconds, further preferably at a temperature of 150° C. or higher to 500° C. or lower. Heating under such conditions can promote the planarization attributable to thermal flow and the crosslinking reaction. In a multilayer resist method, a coating-type silicon middle layer film or a CVD hard mask is sometimes formed on a film obtained as described above. In the case where a coating-type silicon middle layer film is employed, the film formation is performed preferably at a temperature higher than a temperature at which the silicon middle layer film is formed. Generally, a silicon middle layer film is formed at 100° C. or higher to 400° C. or lower, preferably 150° C. or higher to 350° C. or lower. Forming the organic underlayer film at a temperature higher than these temperatures makes it possible to prevent a composition for forming the silicon middle layer film from dissolving the organic underlayer film, and to form an organic film not mixed with the composition.

In the case where a CVD hard mask is employed in the film formation by the 1-stage baking, the organic underlayer film is formed preferably at a temperature higher than a temperature at which the CVD hard mask is formed. Examples of the temperature at which the CVD hard mask is formed include temperatures at 150° C. or higher to 500° C. or lower.

On the other hand, in the film formation by the 2-stage baking, the first baking is performed in air within a temperature range of 50° C. or higher to 300° C. or lower, preferably 250° C. or lower, within 5 to 600 seconds, preferably 10 to 600 seconds, considering the influence of oxygen in air on the substrate corrosion. The second baking temperature under an inert gas atmosphere is higher than the first baking temperature, and the second baking is performed at a temperature of 200° C. or higher to 600° C. or lower, preferably 500° C. or lower, within a range of preferably 10 to 7200 seconds. In a multilayer resist method, a coating-type silicon middle layer film or a CVD hard mask is sometimes formed on a film obtained as described above. In the case where a coating-type silicon middle layer film is employed, the film formation is performed preferably at a temperature higher than a temperature at which the silicon middle layer film is formed. Generally, a silicon middle layer film is formed at 100° C. or higher to 400° C. or lower, preferably 150° C. or higher to 350° C. or lower. Forming the organic underlayer film at a temperature higher than these temperatures by the second baking makes it possible to prevent a composition for forming the silicon middle layer film from dissolving the organic underlayer film, and to form an organic film not mixed with the composition.

In the case where a CVD hard mask is employed in the film formation by the 2-stage baking, the organic underlayer film is formed by the second baking preferably at a temperature higher than a temperature at which the CVD hard mask is formed. Examples of the temperature at which the CVD hard mask is formed include temperatures at 150° C. or higher to 500° C. or lower.

Furthermore, the present invention provides a method for forming an organic film that functions as an organic underlayer film used in a semiconductor apparatus manufacturing process. In order to prevent corrosion of a substrate to be processed, the method includes heating the substrate to be processed under an inert gas atmosphere with an oxygen concentration of 1% or less to thereby form a cured film.

In this method for forming an organic film, first of all, a substrate to be processed is spin-coated with the above-described inventive composition for forming an organic film. After the spin coating, in the film formation by the 2-stage baking, first, baking is performed in air at 50° C. or higher to 300° C. or lower. Then, the second baking is performed under an inert gas atmosphere with an oxygen concentration of 1% or less. In the film formation by the 1-stage baking, the first baking in air in the film formation by the 2-stage baking can be skipped. Note that examples of the atmosphere during the baking include such inert gases as nitrogen, argon, and helium. The inventive composition for forming an organic film is capable of forming a sufficiently cured organic film without generating a sublimation product, even when the baking is performed under such an inert gas atmosphere.

Meanwhile, the inventive methods for forming an organic film make it possible to use a substrate to be processed having a structure or a step with a height of 30 nm or more. As described above, since the inventive composition for forming an organic film is excellent in filling and planarizing properties, even when the substrate to be processed has a structure or a step (asperity) with a height of 30 nm or more, a flat cured film can be formed. Specifically, the inventive method for forming an organic film is particularly useful when a flat organic film is formed on such a substrate to be processed.

Note that the thickness of the organic film to be formed is appropriately selected, but is preferably 30 to 20,000 nm, particularly preferably 50 to 15,000 nm.

Additionally, the above-described methods for forming an organic film are applicable, using the inventive composition for forming an organic film, to both cases where an organic film for an organic underlayer film is formed, and where an organic film for a flat film is formed.

<Patterning Processes>
[3-Layer Resist Method Using Silicon-Containing Resist Middle Layer Film]

The present invention provides a patterning process including:

forming an organic film on a body to be processed from the above-described inventive composition for forming an organic film;

forming a resist middle layer film on the organic film from a resist middle layer film composition containing silicon atoms;

forming a resist upper layer film on the resist middle layer film from a resist upper layer film composition composed of a photoresist composition;

forming a circuit pattern in the resist upper layer film;

transferring the pattern to the resist middle layer film by etching using the resist upper layer film having the formed circuit pattern as a mask;

transferring the pattern to the organic film by etching using the resist middle layer film having the transferred pattern as a mask; and further transferring the pattern to the body to be processed by etching using the organic film having the transferred pattern as a mask.

As the body to be processed, it is preferable to use a semiconductor apparatus substrate or the semiconductor apparatus substrate coated with any of a metal film, a metal carbide film, a metal oxide film, a metal nitride film, a metal oxycarbide film, and a metal oxynitride film. More specifically, examples of the body which may be used include, but are not particularly limited to: substrates made of Si, α-Si, p-Si, $SiO_2$, SiN, SiON, W, TiN, Al, or the like; and these substrates coated with the above-described metal film or the like as a layer to be processed.

As the layer to be processed, used are various Low-k films made of Si, $SiO_2$, SiON, SiN, p-Si, α-Si, W, W—Si, Al, Cu, Al—Si, or the like, and stopper films thereof. The layer can be formed to have a thickness of generally 50 to 10,000 nm, particularly 100 to 5,000 nm. Note that when the layer to be processed is formed, the substrate and the layer to be processed are formed from different materials.

Note that the metal of the body to be processed is preferably silicon, titanium, tungsten, hafnium, zirconium, chromium, germanium, copper, silver, gold, aluminum, indium, gallium, arsenic, palladium, iron, tantalum, iridium, molybdenum, or an alloy thereof.

When the organic film is formed on the body to be processed from the inventive composition for forming an organic film, the above-described inventive methods for forming an organic film can be employed.

Next, using a resist middle layer film composition containing silicon atoms, a resist middle layer film (silicon-containing resist middle layer film) is formed on the organic film. The silicon-containing resist middle layer film composition is preferably a polysiloxane-based middle layer film composition. The silicon-containing resist middle layer film having antireflective effect can suppress the reflection. Particularly, for 193-nm light exposure, a composition containing many aromatic groups and having a high etching selectivity relative to the substrate is used as a composition for forming an organic film, so that the k-value and thus the substrate reflection are increased; in contrast, the reflection can be suppressed by imparting absorption to the silicon-containing resist middle layer film so as to have an appropriate k-value, and the substrate reflection can be reduced to 0.5% or less. As the silicon-containing resist middle layer film having antireflective effect, a polysiloxane is preferably used which has anthracene for 248-nm and 157-nm light exposure, or a phenyl group or a light-absorbing group having a silicon-silicon bond for 193-nm light exposure in a pendant structure or a polysiloxane structure, and which is crosslinked by an acid or heat.

Next, using a resist upper layer film composition composed of a photoresist composition, a resist upper layer film is formed on the silicon-containing resist middle layer film. The resist upper layer film composition may be a positive type or a negative type, and any generally-used photoresist composition can be used. After the spin coating of the resist upper layer film composition, pre-baking is preferably performed within ranges of 60 to 180° C. and 10 to 300 seconds. Then, light exposure, post-exposure bake (PEB), and development are performed according to conventional methods to obtain a resist upper layer film pattern. Note that the thickness of the resist upper layer film is not particularly limited, but is preferably 30 to 500 nm, particularly preferably 50 to 400 nm.

Next, a circuit pattern (the resist upper layer film pattern) is formed in the resist upper layer film. The circuit pattern is preferably formed by a lithography using light with a wavelength ranging from 10 nm to 300 nm, a direct drawing by electron beam, a nanoimprinting, or a combination thereof.

Note that the exposure light includes high energy beam with a wavelength of 300 nm or less; specifically, deep ultraviolet ray, KrF excimer laser beam (248 nm), ArF excimer laser beam (193 nm), $F_2$ laser beam (157 nm), $Kr_2$ laser beam (146 nm), $Ar_2$ laser beam (126 nm), soft X-ray (EUV) with a wavelength of 3 to 20 nm, electron beam (EB), ion beam, X-ray, and the like.

Additionally, in forming the circuit pattern, the circuit pattern is preferably developed by alkaline development or development with an organic solvent.

Next, using the resist upper layer film having the formed circuit pattern as a mask, the pattern is transferred to the silicon-containing resist middle layer film by etching. The etching of the silicon-containing resist middle layer film using the resist upper layer film pattern as a mask is preferably performed with a fluorocarbon-based gas. Thereby, a silicon-containing resist middle layer film pattern is formed.

Next, using the silicon-containing resist middle layer film having the transferred pattern as a mask, the pattern is transferred to the organic film by etching. Since the silicon-containing resist middle layer film exhibits higher etching resistance to an oxygen gas or a hydrogen gas than an organic compound, the etching of the organic film using the silicon-containing resist middle layer film pattern as a mask is preferably performed with an etching gas mainly containing an oxygen gas or a hydrogen gas. Thereby, an organic film pattern is formed.

Next, using the organic film having the transferred pattern as a mask, the pattern is transferred to the body to be processed by etching. The subsequent etching of the body to be processed (layer to be processed) can be performed according to a conventional method. For example, the body to be processed made of $SiO_2$, SiN, or silica low-dielectric insulating film is etched mainly with a fluorocarbon-based gas. The body to be processed made of p-Si, Al, or W is etched mainly with a chlorine- or bromine-based gas. When the substrate is processed by etching with a fluorocarbon-based gas, the silicon-containing resist middle layer film pattern is removed together with the substrate processing. Meanwhile, when the substrate is processed by etching with a chlorine- or bromine-based gas, the silicon-containing resist middle layer film pattern needs to be removed by additional dry etching with a fluorocarbon-based gas after the substrate processing.

The organic film obtained from the inventive composition for forming an organic film can exhibit excellent etching resistance when the body to be processed is etched as described above.

[4-Layer Resist Method Using Silicon-Containing Resist Middle Layer Film and Organic Antireflective Film]

Moreover, the present invention provides a patterning process including:

forming an organic film on a body to be processed from the above-described inventive composition for forming an organic film;

forming a silicon-containing resist middle layer film on the organic film from a resist middle layer film composition containing silicon atoms;

forming an organic antireflective film on the silicon-containing resist middle layer film;

forming a resist upper layer film on the organic antireflective film from a resist upper layer film composition composed of a photoresist composition; forming a circuit pattern in the resist upper layer film;

transferring the pattern to the organic antireflective film and the silicon-containing resist middle layer film by etching using the resist upper layer film having the formed circuit pattern as a mask;

transferring the pattern to the organic film by etching using the silicon-containing resist middle layer film having the transferred pattern as a mask; and further transferring the pattern to the body to be processed by etching using the organic film having the transferred pattern as a mask.

Note that this method can be performed in the same manner as the above-described 3-layer resist method using the silicon-containing resist middle layer film, except that the organic antireflective film (BARC) is formed between the silicon-containing resist middle layer film and the resist upper layer film.

The organic antireflective film can be formed by spin coating from a known organic antireflective film composition.

[3-Layer Resist Method Using Inorganic Hard Mask]

Further, the present invention provides a patterning process according to a 3-layer resist method using the above-described inventive composition for forming an organic film, including:

forming an organic film on a body to be processed from the inventive composition for forming an organic film;

forming an inorganic hard mask selected from a silicon oxide film, a silicon nitride film, a silicon oxynitride film, a titanium oxide film, and a titanium nitride film on the organic film;

forming a resist upper layer film on the inorganic hard mask from a resist upper layer film composition composed of a photoresist composition;

forming a circuit pattern in the resist upper layer film;

transferring the pattern to the inorganic hard mask by etching using the resist upper layer film having the formed circuit pattern as a mask;

transferring the pattern to the organic film by etching using the inorganic hard mask having the transferred pattern as a mask; and further transferring the pattern to the body to be processed by etching using the organic film having the transferred pattern as a mask.

Note that this method can be performed in the same manner as the above-described 3-layer resist method using the silicon-containing resist middle layer film, except that the inorganic hard mask is formed in place of the silicon-containing resist middle layer film on the organic film.

The inorganic hard mask selected from a silicon oxide film, a silicon nitride film, a silicon oxynitride film (SiON film), a titanium oxide film, and a titanium nitride film can be formed by a CVD method, an ALD method, or the like.

The method for forming the silicon nitride film is disclosed in, for example, Japanese Patent Laid-Open Publication No. 2002-334869, International Publication No. 2004/066377, and so forth. The film thickness of the inorganic hard mask is preferably 5 to 200 nm, more preferably 10 to 100 nm. As the inorganic hard mask, a SiON film is most preferably used which is effective as an antireflective film. When the SiON film is formed, the substrate temperature reaches 300 to 500° C. Hence, the underlayer film needs to withstand the temperature of 300 to 500° C. Since the organic film formed from the inventive composition for forming an organic film has high heat resistance and can withstand high temperatures of 300° C. to 500° C., this enables the combination of the inorganic hard mask formed by a CVD method or an ALD method with the organic film formed by a spin coating method.

[4-Layer Resist Method Using Inorganic Hard Mask and Organic Antireflective Film]

Furthermore, the present invention provides a patterning process according to a 4-layer resist method using the above-described inventive composition for forming an organic film, including:

forming an organic film on a body to be processed from the inventive composition for forming an organic film;

forming an inorganic hard mask selected from a silicon oxide film, a silicon nitride film, a silicon oxynitride film, a titanium oxide film, and a titanium nitride film on the organic film;

forming an organic antireflective film on the inorganic hard mask;

forming a resist upper layer film on the organic antireflective film from a resist upper layer film composition composed of a photoresist composition;

forming a circuit pattern in the resist upper layer film;

transferring the pattern to the organic antireflective film and the inorganic hard mask by etching using the resist upper layer film having the formed circuit pattern as a mask;

transferring the pattern to the organic film by etching using the inorganic hard mask having the transferred pattern as a mask; and further transferring the pattern to the body to be processed by etching using the organic film having the transferred pattern as a mask.

Note that this method can be performed in the same manner as the above-described 3-layer resist method using the inorganic hard mask, except that the organic antireflective film (BARC) is formed between the inorganic hard mask and the resist upper layer film.

Particularly, when the SiON film is used as the inorganic hard mask, two antireflective films including the SiON film and the BARC make it possible to suppress the reflection even in liquid immersion exposure at a high NA exceeding 1.0. Another merit of the BARC formation is having an effect of reducing footing of the resist upper layer film pattern immediately above the SiON film.

Figure 2:
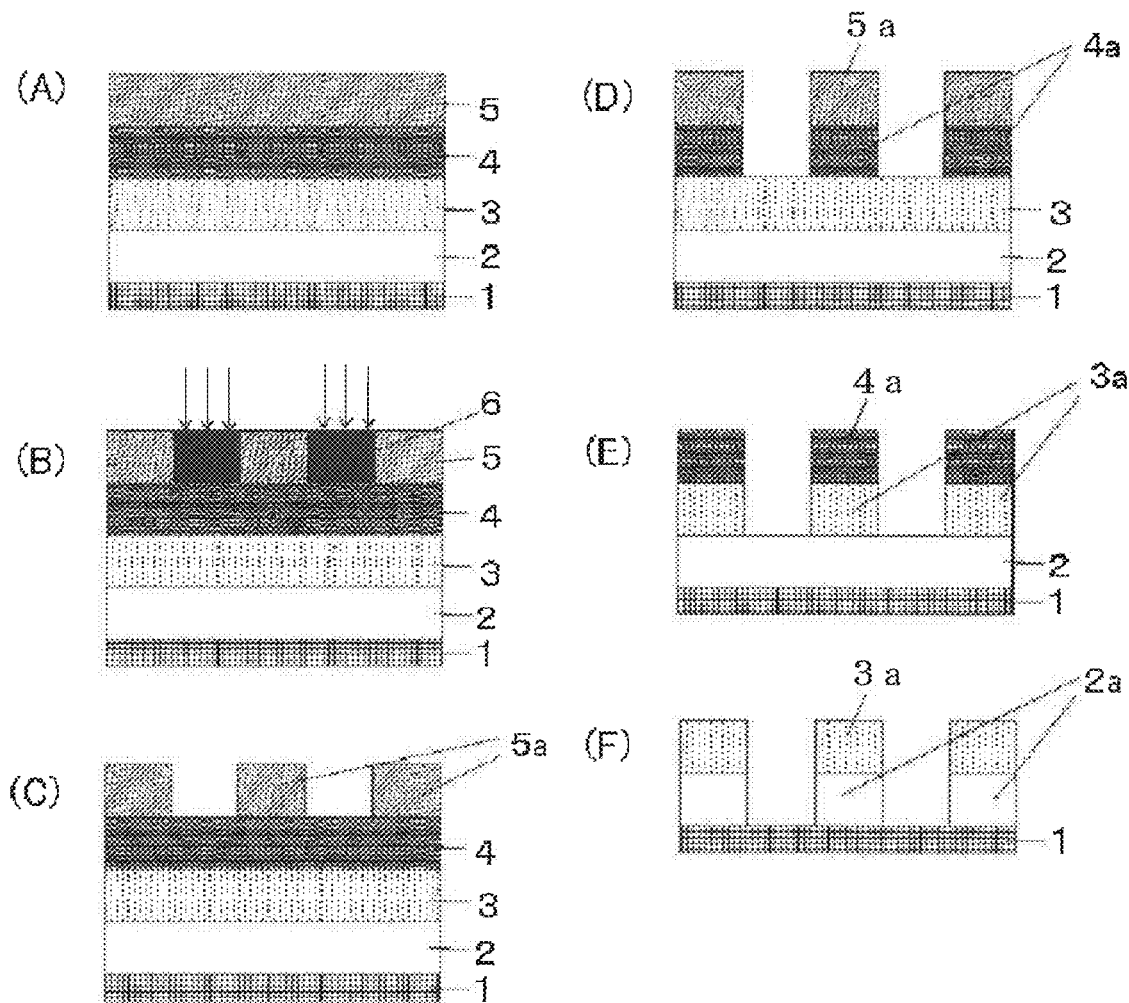
FIG. 2 is an explanatory view of an example of an inventive patterning process according to a 3-layer resist method.

Herein, FIG. 2 (A) to (F) show an example of the inventive patterning process according to the 3-layer resist method. In the 3-layer resist method as shown in FIG. 2 (A), using the inventive composition for forming an organic film, an organic film 3 is formed on a layer to be processed 2 formed on a substrate 1. Then, a silicon-containing resist middle layer film 4 is formed on the organic film 3, and a resist upper layer film 5 is formed on the silicon-containing resist middle layer film 4. Subsequently, as shown in FIG. 2 (B), an exposed portion 6 of the resist upper layer film 5 is exposed to light, followed by PEB (post-exposure bake).

Thereafter, as shown in FIG. 2 (C), a resist upper layer film pattern 5a is formed by development. After that, as shown in FIG. 2 (D), using the resist upper layer film pattern 5a as a mask, the silicon-containing resist middle layer film 4 is processed by dry etching with a fluorocarbon-based gas. Thereby, a silicon-containing resist middle layer film pattern 4a is formed. Then, as shown in FIG. 2 (E), after the resist upper layer film pattern 5a is removed, the organic film 3 is etched with oxygen plasma using the silicon-containing resist middle layer film pattern 4a as a mask. Thereby, an organic film pattern 3a is formed. Further, as shown in FIG. 2 (F), after the silicon-containing resist middle layer film pattern 4a is removed, the layer to be processed 2 is processed by etching using the organic film pattern 3a as a mask. Thus, a pattern 2a is formed.

In the case where an inorganic hard mask is formed, the silicon-containing resist middle layer film 4 may be replaced with the inorganic hard mask. In the case where a BARC is formed, the BARC may be formed between the silicon-containing resist middle layer film 4 and the resist upper layer film 5. The BARC may be etched continuously and before the etching of the silicon-containing resist middle layer film 4. Alternatively, after the BARC is etched alone, the silicon-containing resist middle layer film 4 may be etched, for example, after an etching apparatus is changed.

As described above, the inventive patterning processes make it possible to precisely form a fine pattern in a body to be processed by the multilayer resist methods.

EXAMPLES

Hereinafter, the present invention will be more specifically described by referring to Synthesis Examples, Comparative Synthesis Examples, Examples, and Comparative Examples. However, the present invention is not limited thereto. Note that, with respect to molecular weight and dispersity, weight average molecular weight (Mw) and number average molecular weight (Mn) were measured by gel permeation chromatography (GPC) using tetrahydrofuran as an eluent in terms of polystyrene, and dispersity (Mw/Mn) was calculated therefrom.

Synthesis Examples: Synthesis of Compounds Used in Composition for Forming Organic Film Compounds (A1) to (A22) used in a composition for forming an organic film were synthesized using compounds P: (P1) to (P12) and compounds Q: (Q1) to (Q5) shown below.

Compounds P: Nitrogen-Containing Compounds

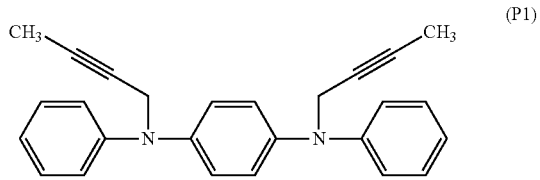

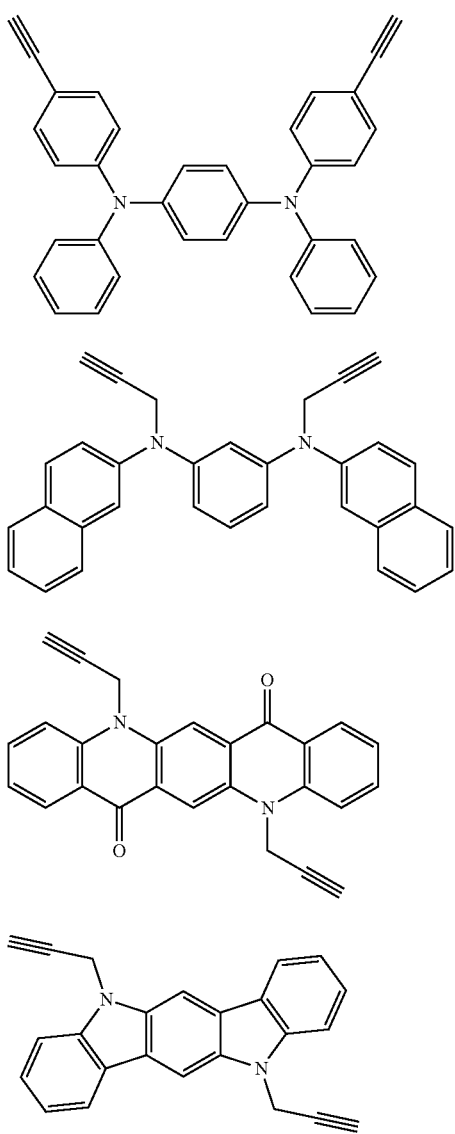
Compounds Q: Aldehyde or Ketone Compounds

-continued

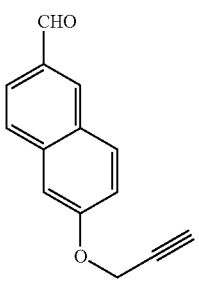

(Q4)

(Q5)

Incidentally, as formaldehyde shown by (Q1), a 37% formalin aqueous solution was used.

[Synthesis Example 1] Synthesis of Compound (A1)

(A1)

A homogeneous solution was formed from 84.9 g of (P1), 15.1 g of the 37% formalin aqueous solution (Q1), 5 ml of 3-mercaptopropionic acid, and 300 ml of 1,2-dichloroethane under a nitrogen atmosphere at an inner temperature of 70° C. Then, 10 ml of methanesulfonic acid was slowly added to the homogeneous solution, and the reaction was allowed to proceed at an inner temperature of 70° C. for 24 hours. After cooling to room temperature, 500 g of methyl isobutyl ketone was added thereto, and the organic layer was washed five times with 100 g of pure water. Subsequently, the organic layer was evaporated under reduced pressure to dryness. To the residue, 200 g of THF was added, and a homogeneous solution was formed. Thereafter, the polymer was reprecipitated with 1500 g of methanol. The precipitated polymer was separated by filtration, washed twice with 800 g of methanol, and collected. The collected polymer was vacuum dried at 70° C. Thus, (A1) was obtained.

When the weight average molecular weight (Mw) and dispersity (Mw/Mn) were measured by GPC, the following results were obtained.

(A1): Mw=2800, Mw/Mn=2.76

[Synthesis Examples 2 to 20] Synthesis of Compounds (A2) to (A20)

Compounds (A2) to (A20) as shown in Table 1 were obtained as products under the same reaction conditions as those in Synthesis Example 1, except that the compounds P and the compounds Q shown in Table 1 were used. The weight average molecular weight (Mw) and dispersity (Mw/Mn) of these compounds were measured and shown in Tables 2 and 3.

TABLE 1

| Synthesis Example | Compounds P | Compounds Q | Product |
|---|---|---|---|
| 1 | P1: 84.9 g | Q1: 15.1 g | A1 |
| 2 | P1: 74.5 g | Q3: 25.5 g | A2 |
| 3 | P2: 84.4 g | Q2: 15.6 g | A3 |
| 4 | P2: 76.2 g | Q5: 23.8 g | A4 |
| 5 | P3: 72.2 g | Q4: 27.8 g | A5 |
| 6 | P3: 75.2 g | Q5: 24.8 g | A6 |
| 7 | P4: 88.3 g | Q1: 11.7 g | A7 |
| 8 | P4: 79.6 g | Q3: 20.4 g | A8 |
| 9 | P5: 79.7 g | Q2: 20.3 g | A9 |
| 10 | P5: 69.7 g | Q5: 30.3 g | A10 |
| 11 | P6: 68.2 g | Q4: 31.8 g | A11 |
| 12 | P6: 71.4 g | Q5: 28.6 g | A12 |
| 13 | P5: 71.2 g | Q3: 13.4 g | A13 |
|  |  | Q5: 15.4 g |  |
| 14 | P3: 25.8 g | Q5: 28.4 g | A14 |
|  | P6: 45.8 g |  |  |
| 15 | P7: 80.1 g | Q1: 19.9 g | A15 |
| 16 | P8: 82.9 g | Q2: 17.1 g | A16 |
| 17 | P9: 71.4 g | Q5: 28.6 g | A17 |
| 18 | P10: 71.4 g | Q3: 28.6 g | A18 |
| 19 | P11: 64.0 g | Q5: 36.0 g | A19 |
| 20 | P12: 64.0 g | Q5: 36.0 g | A20 |

TABLE 2

| Synthesis Example | Compound | Mw (GPC) | Mw/Mn |
|---|---|---|---|
| 1 | 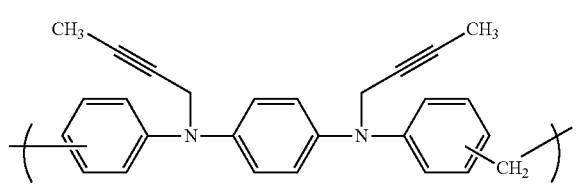 (A1) | 2800 | 2.76 |

TABLE 2-continued
| Synthesis Example | Compound | Mw (GPC) | Mw/Mn |
|---|---|---|---|
| 2 | 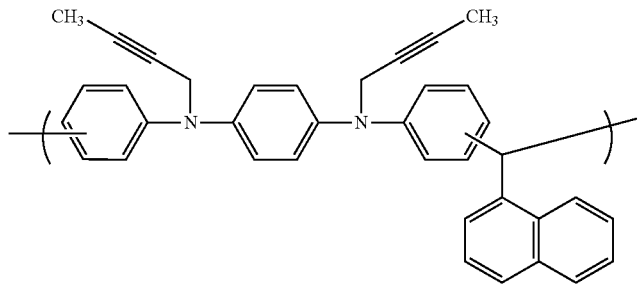 (A2) | 3100 | 2.73 |
| 3 | 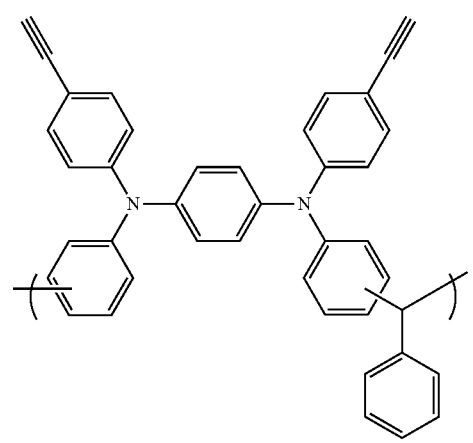 (A3) | 2500 | 2.13 |
| 4 | 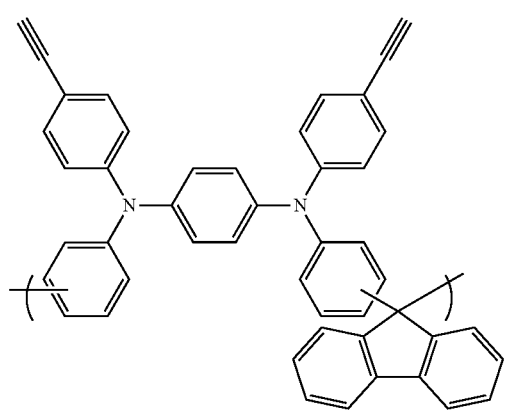 (A4) | 3600 | 3.10 |

TABLE 2-continued
| Synthesis Example | Compound | Mw (GPC) | Mw/Mn |
|---|---|---|---|
| 5 | 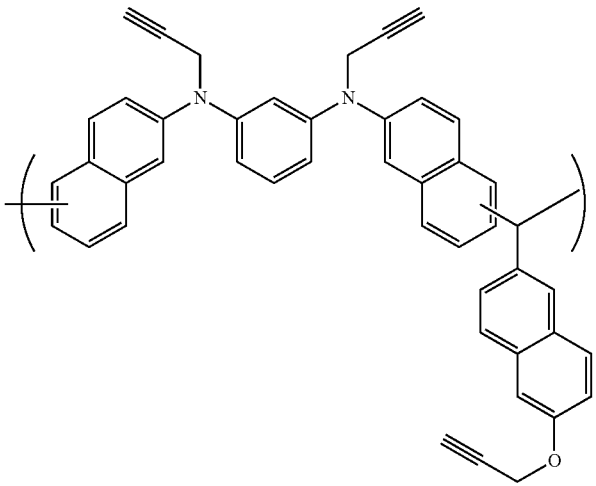 (A5) | 3800 | 3.01 |
| 6 | 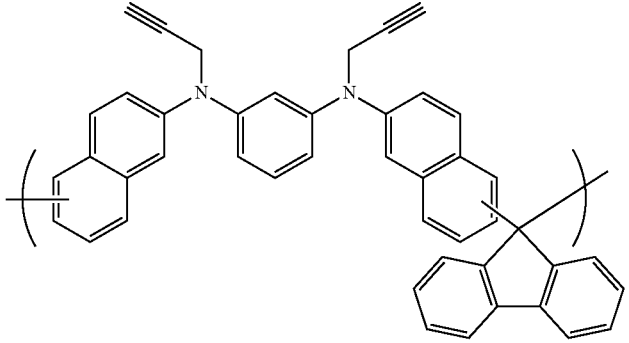 (A6) | 3200 | 2.78 |
| 7 | 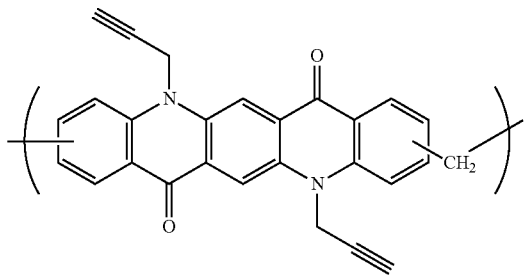 (A7) | 3100 | 2.64 |

TABLE 2-continued
| Synthesis Example | Compound | Mw (GPC) | Mw/Mn |
|---|---|---|---|
| 8 | 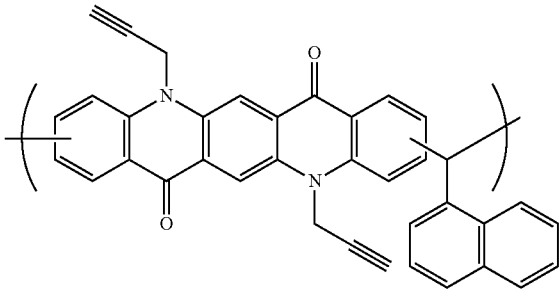<br>(A8) | 2900 | 2.49 |
| 9 | 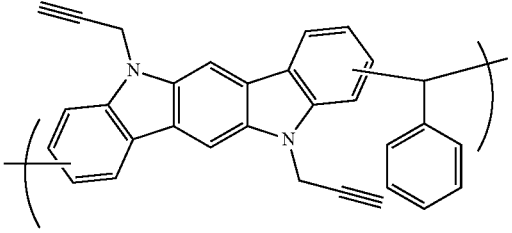<br>(A9) | 2800 | 2.84 |
| 10 | 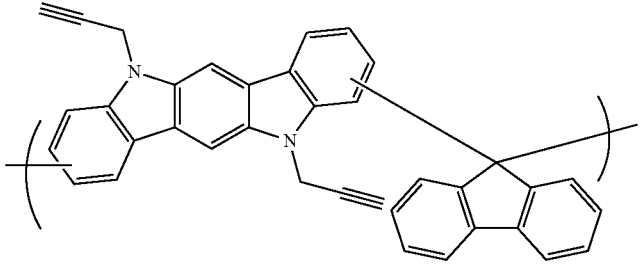<br>(A10) | 3600 | 2.87 |

TABLE 3
| Synthesis Example | Compound | Mw (GPC) | Mw/Mn |
|---|---|---|---|
| 11 | 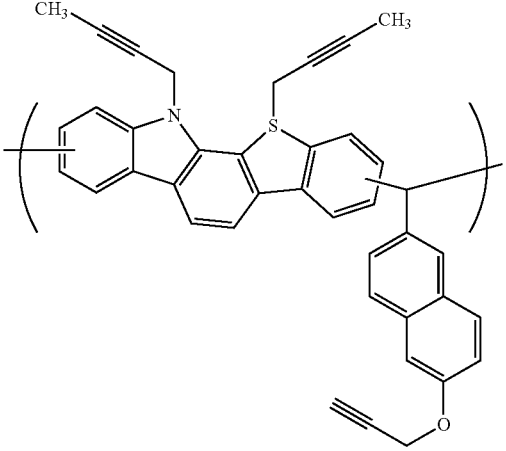(A11) | 2500 | 2.54 |
| 12 | 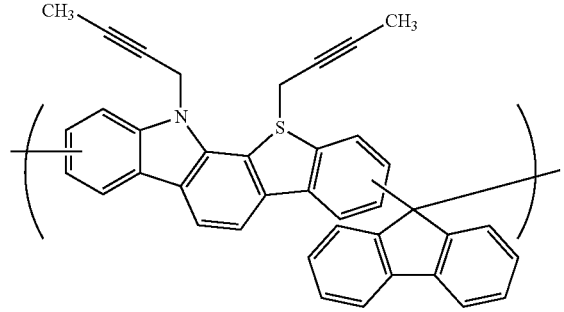(A12) | 3100 | 2.93 |
| 13 | 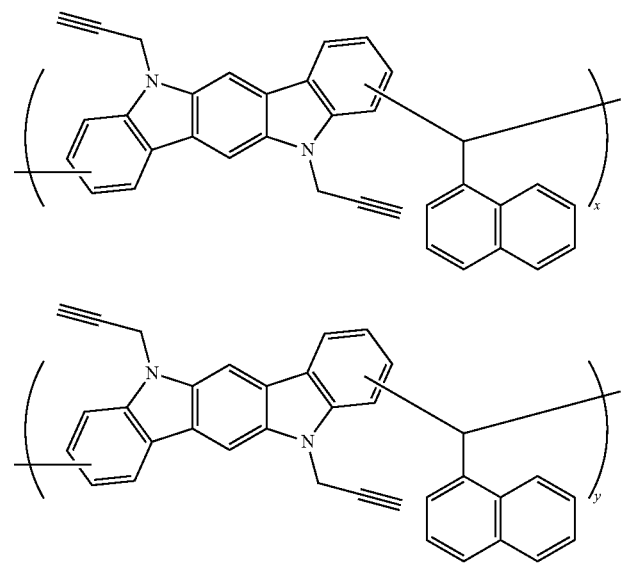x:y = 50:50 (A13) | 3300 | 2.84 |

TABLE 3-continued
| Synthesis Example | Compound | Mw (GPC) | Mw/Mn |
|---|---|---|---|
| 14 | 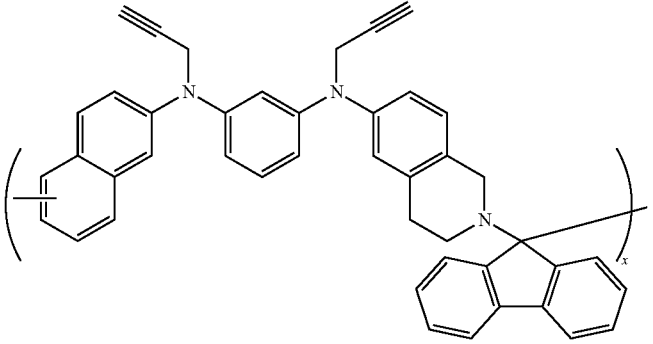<br>x:y = 30:70<br>(A14) | 3400 | 3.28 |
| 15 | 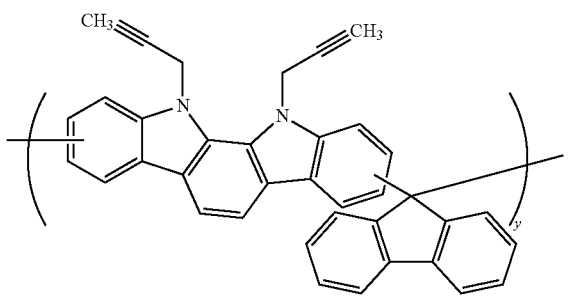<br>(A15) | 2700 | 2.78 |
| 16 | 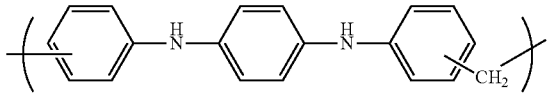<br>(A16) | 2600 | 2.46 |

TABLE 3-continued

| Synthesis Example | Compound | Mw (GPC) | Mw/Mn |
|---|---|---|---|
| 17 | (A17) | 3400 | 2.69 |
| 18 | (A18) | 3100 | 2.87 |
| 19 | (A19) | 3400 | 2.75 |
| 20 | (A20) | 3200 | 2.92 |

[Synthesis Example 21] Synthesis of Compound (A21)

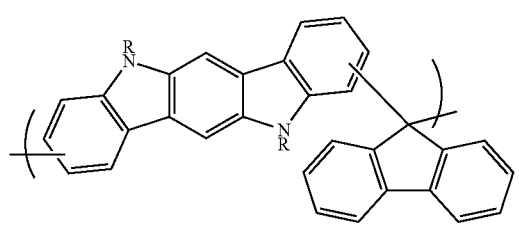

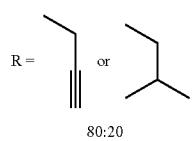

80:20

A homogeneous dispersion was formed from 30.0 g of the compound (A19) synthesized in Synthesis Example 19, 1.3 g of tetrabutylammonium iodide, 86.0 g of a 25% sodium hydroxide aqueous solution, and 150 g of tetrahydrofuran under a nitrogen atmosphere at an inner temperature of 50° C. A mixture solution of 4.9 g of isobutyl bromide and 17.1 g of propargyl bromide was slowly added dropwise to the homogeneous dispersion, and the reaction was allowed to proceed at an inner temperature of 50° C. for 12 hours. After cooling to room temperature, 300 g of methyl isobutyl ketone was added thereto, and the aqueous layer was removed. Further, the organic layer was washed twice with 80 g of a 3.0% nitric acid aqueous solution and five times with 80 g of pure water. The organic layer was evaporated under reduced pressure to dryness. To the residue, 100 g of THF was added, and the polymer was reprecipitated with 800 g of methanol. The precipitated polymer was separated by filtration, washed twice with 400 g of methanol, and collected. The collected polymer was vacuum dried at 70° C. Thus, (A21) was obtained.

When the weight average molecular weight (Mw) and dispersity (Mw/Mn) were measured by GPC, the following results were obtained.
(A21): Mw=3800, Mw/Mn=2.63

[Synthesis Example 22] Synthesis of Compound (A22)

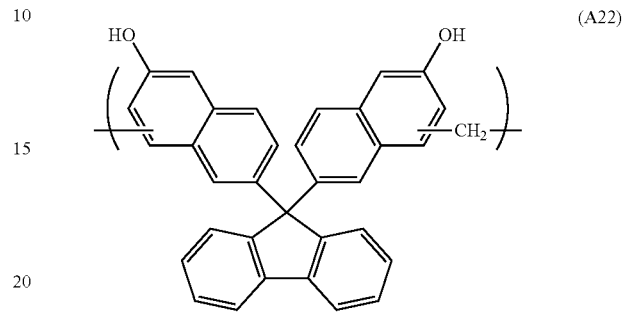

A homogeneous solution was formed from 90.1 g of 9,9-fluorenylidene-bisnaphthol, 10.5 g of the 37% formalin aqueous solution, and 270 g of 2-methoxy-1-propanol under a nitrogen atmosphere at an inner temperature of 80° C. Then, 18 g of a 2-methoxy-1-propanol solution containing 20% p-toluenesulfonic acid was slowly added to the homogeneous solution, and stirred at an inner temperature of 110° C. for 8 hours. After cooling to room temperature, 600 g of methyl isobutyl ketone was added thereto, and the organic layer was washed five times with 200 g of pure water. Subsequently, the organic layer was evaporated under reduced pressure to dryness. To the residue, 400 ml of THF was added, and the polymer was reprecipitated with 2,000 ml of hexane. The precipitated polymer was separated by filtration and dried under reduced pressure. Thus, a compound (A22) was obtained.

When the weight average molecular weight (Mw) and dispersity (Mw/Mn) were measured by GPC, the following results were obtained.
(A22): Mw=3700, Mw/Mn=2.82

Preparation of Compositions (UDL-1 to -20, Comparative UDL-1 to -14) for Forming Organic Film The compounds (A1) to (A22) synthesized in Synthesis Examples, a crosslinking agent (CR1) and an acid generator (AG1) as additives, and (S1) 1,6-diacetoxyhexane having a boiling point of 260° C. or (S2) tripropylene glycol monomethyl ether having a boiling point of 242° C. as a high-boiling-point solvent were dissolved in a solvent containing propylene glycol monomethyl ether acetate (PGMEA) and 0.1 mass % FC-4430 (manufactured by Sumitomo 3M Ltd.) in proportions shown in Table 4. The solution was filtered through a 0.1-μm filter made of a fluorinated resin to prepare compositions (UDL-1 to -20, comparative UDL-1 to -14) for forming an organic film.

TABLE 4

| Composition for forming organic film | Compound (1) (part by mass) | Crosslinking agent (part by mass) | High-boiling-point solvent (part by mass) | Acid generator (part by mass) | PGMEA (part by mass) |
|---|---|---|---|---|---|
| UDL-1 | A1 (10) | — | — | — | 90 |
| UDL-2 | A2 (10) | — | — | — | 90 |
| UDL-3 | A3 (10) | — | — | — | 90 |
| UDL-4 | A4 (10) | — | — | — | 90 |
| UDL-5 | A5 (10) | — | — | — | 90 |
| UDL-6 | A6 (10) | — | — | — | 90 |
| UDL-7 | A7 (10) | — | — | — | 90 |

TABLE 4-continued

| Composition for forming organic film | Compound (1) (part by mass) | Crosslinking agent (part by mass) | High-boiling-point solvent (part by mass) | Acid generator (part by mass) | PGMEA (part by mass) |
|---|---|---|---|---|---|
| UDL-8 | A8 (10) | — | — | — | 90 |
| UDL-9 | A9 (10) | — | — | — | 90 |
| UDL-10 | A10 (10) | — | — | — | 90 |
| UDL-11 | A11 (10) | — | — | — | 90 |
| UDL-12 | A12 (10) | — | — | — | 90 |
| UDL-13 | A13 (10) | — | — | — | 90 |
| UDL-14 | A14 (10) | — | — | — | 90 |
| UDL-15 | A21 (10) | — | — | — | 90 |
| UDL-16 | A6 (5) A10 (5) | — | — | — | 90 |
| UDL-17 | A6 (10) | — | S1 (10) | — | 80 |
| UDL-18 | A10 (10) | — | S1 (10) | — | 80 |
| UDL-19 | A6 (10) | — | S2 (10) | — | 80 |
| UDL-20 | A10 (10) | — | S2 (10) | — | 80 |
| comparative UDL-1 | A15 (10) | — | — | — | 90 |
| comparative UDL-2 | A15 (10) | CR1 (2) | — | AG1 (0.5) | 90 |
| comparative UDL-3 | A16 (10) | — | — | — | 90 |
| comparative UDL-4 | A16 (10) | CR1 (2) | — | AG1 (0.5) | 90 |
| comparative UDL-5 | A17 (10) | — | — | — | 90 |
| comparative UDL-6 | A17 (10) | CR1 (2) | — | AG1 (0.5) | 90 |
| comparative UDL-7 | A18 (10) | — | — | — | 90 |
| comparative UDL-8 | A18 (10) | CR1 (2) | — | AG1 (0.5) | 90 |
| comparative UDL-9 | A19 (10) | — | — | — | 90 |
| comparative UDL-10 | A19 (10) | CR1 (2) | — | AG1 (0.5) | 90 |
| comparative UDL-11 | A20 (10) | — | — | — | 90 |
| comparative UDL-12 | A20 (10) | CR1 (2) | — | AG1 (0.5) | 90 |
| comparative UDL-13 | A22 (10) | — | — | — | 90 |
| comparative UDL-14 | A22 (10) | CR1 (2) | — | AG1 (0.5) | 90 |

The crosslinking agent (CR1) and the acid generator (AG1) used are shown below.

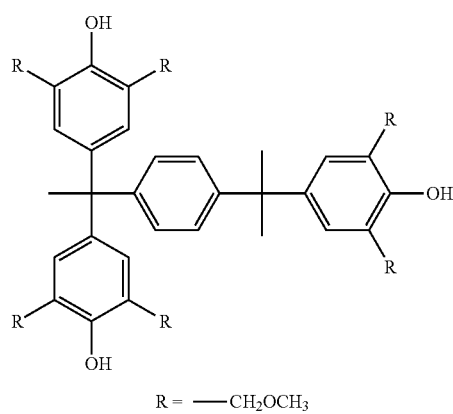

(CR1)

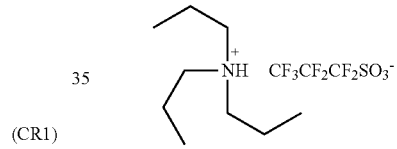

(AG1)

Example 1: Solvent Resistance Measurement (Examples 1-1 to 1-10, Comparative Examples 1-1 to 1-14)

The compositions (UDL-1 to -20, comparative UDL-1 to -14) for forming an organic film prepared above were each applied onto a silicon substrate and baked at 400° C. for 60 seconds under such a nitrogen stream that the oxygen concentration was controlled to 0.2% or less. Then, the film thickness was measured. A PGMEA solvent was dispensed on the film and allowed to stand for 30 seconds. The resultant was spin dried and baked at 100° C. for 60 seconds to evaporate the PGMEA. The film thickness was measured to find a difference in the film thicknesses before and after the PGMEA treatment. Table 5 shows these results.

TABLE 5

|  | Composition for forming organic film | Film thickness after film formation: a (Å) | Film thickness after PGMEA formation: b (Å) | (b/a) × 100 (%) |
|---|---|---|---|---|
| Ex. 1-1 | UDL-1 | 3008 | 3005 | 99.9 |
| Ex. 1-2 | UDL-2 | 3009 | 3004 | 99.8 |
| Ex. 1-3 | UDL-3 | 2999 | 2998 | 100.0 |
| Ex. 1-4 | UDL-4 | 2978 | 2976 | 99.9 |
| Ex. 1-5 | UDL-5 | 2989 | 2989 | 100.0 |
| Ex. 1-6 | UDL-6 | 3001 | 2998 | 99.9 |
| Ex. 1-7 | UDL-7 | 3021 | 3017 | 99.9 |
| Ex. 1-8 | UDL-8 | 2998 | 2997 | 100.0 |

TABLE 5-continued

| | Composition for forming organic film | Film thickness after film formation: a (Å) | Film thickness after PGMEA formation: b (Å) | (b/a) × 100 (%) |
|---|---|---|---|---|
| Ex. 1-9 | UDL-9 | 2978 | 2975 | 99.9 |
| Ex. 1-10 | UDL-10 | 2991 | 2985 | 99.8 |
| Ex. 1 11 | UDL-11 | 3010 | 3008 | 99.9 |
| Ex. 1-12 | UDL-12 | 3018 | 3015 | 99.9 |
| Ex. 1-13 | UDL-13 | 3011 | 3009 | 99.9 |
| Ex. 1-14 | UDL-14 | 3011 | 3004 | 99.8 |
| Ex. 1-15 | UDL-15 | 3014 | 3010 | 99.9 |
| Ex. 1-16 | UDL-16 | 3008 | 3006 | 99.9 |
| Ex. 1-17 | UDL-17 | 3003 | 3000 | 99.9 |
| Ex. 1-18 | UDL-18 | 2997 | 2997 | 100.0 |
| Ex. 1-19 | UDL-19 | 2998 | 2995 | 99.9 |
| Ex. 1-20 | UDL-20 | 2988 | 2985 | 99.9 |
| Com. Ex. 1-1 | comparative UDL-1 | 2989 | 1436 | 48.0 |
| Com. Ex. 1-2 | comparative UDL-2 | 3001 | 2994 | 99.8 |
| Com. Ex. 1-3 | comparative UDL-3 | 3002 | 1476 | 49.2 |
| Com. Ex. 1-4 | comparative UDL-4 | 2987 | 2983 | 99.9 |
| Com. Ex. 1-5 | comparative UDL-5 | 3004 | 1376 | 45.8 |
| Com. Ex. 1-6 | comparative UDL-6 | 2998 | 2994 | 99.9 |
| Com. Ex. 1-7 | comparative UDL-7 | 2994 | 1298 | 43.4 |
| Com. Ex. 1-8 | comparative UDL-8 | 3000 | 2995 | 99.8 |
| Com. Ex. 1-9 | comparative UDL-9 | 2996 | 1332 | 44.5 |
| Com. Ex. 1-10 | comparative UDL-10 | 3016 | 3013 | 99.9 |
| Com. Ex. 1-11 | comparative UDL-11 | 2987 | 1387 | 46.4 |
| Com. Ex. 1-12 | comparative UDL-12 | 2998 | 2993 | 99.8 |
| Com. Ex. 1-13 | comparative UDL-13 | 3018 | 1237 | 41.0 |
| Com. Ex. 1-14 | comparative UDL-14 | 3009 | 3006 | 99.9 |

As shown in Table 5, in Examples 1-1 to 1-20 using the inventive compositions for forming an organic film, the film remaining percentages after the PGMEA treatment were 99% or more. This indicates that the crosslinking reaction took place even under the nitrogen atmosphere, and sufficient solvent resistance was exhibited. In contrast, among Comparative Examples 1-1 to 1-14, in Comparative Examples 1-1, 1-3, 1-5, 1-7, 1-9, 1-11, and 1-13 in which the crosslinking agent and the thermal acid generator were not added, the film remaining percentages after the PGMEA treatment were all less than 50%, and sufficient solvent resistance was not exhibited. In order for solvent resistance to be exhibited, a crosslinking agent and a thermal acid generator need to be added. This result indicates that the thermosetting reaction occurred by the structure containing the triple bond represented by Y of the present invention, the solvent resistance was exhibited, and the cured film was formed.

Example 2: Heat Resistance Evaluation (Examples 2-1 to 2-20, Comparative Examples 2-1 to 2-20)

The compositions (UDL-1 to -20, comparative UDL-1 to -14) for forming an organic film prepared above were each applied onto a silicon substrate and baked in the atmosphere at 180° C. to form a coating film of 300 nm. The film thickness was measured. This substrate was further baked at 450° C. under such a nitrogen stream that the oxygen concentration was controlled to 0.2% or less. Then, the film thickness was measured (Examples 2-1 to 2-20, Comparative Examples 2-1 to 2-14). Further, the compositions (comparative UDL-1, 3, 5, 7, 9, 11) for forming an organic film were used and baked in the atmosphere at 180° C. in the same manner described above, but subsequently baked in the atmosphere at 450° C. Then, the film thickness was measured (Comparative Examples 2-15 to 2-20). Table 6 shows these results.

TABLE 6

| | Composition for forming organic film | Film thickness at 180° C.: A (Å) | Film thickness at 450° C.: B (Å) | (B/A) × 100 (%) |
|---|---|---|---|---|
| Ex. 2-1 | UDL-1 | 3008 | 2985 | 99.2 |
| Ex. 2-2 | UDL-2 | 3006 | 2984 | 99.3 |
| Ex. 2-3 | UDL-3 | 2999 | 2991 | 99.7 |
| Ex. 2-4 | UDL-4 | 3015 | 2990 | 99.2 |
| Ex. 2-5 | UDL-5 | 3002 | 2990 | 99.6 |
| Ex. 2-6 | UDL-6 | 3013 | 2993 | 99.3 |
| Ex. 2-7 | UDL-7 | 3015 | 2988 | 99.1 |
| Ex- 2-8 | UDL-8 | 3018 | 3003 | 99.5 |
| Ex. 2-9 | UDL-9 | 3017 | 3002 | 99.5 |
| Ex. 2-10 | UDL-10 | 2994 | 2983 | 99.6 |
| Ex. 2-11 | UDL-11 | 3008 | 2997 | 99.6 |
| Ex. 2-12 | UDL-12 | 2994 | 2984 | 99.7 |
| Ex. 2-13 | UDL-13 | 3017 | 2993 | 99.2 |
| Ex. 2-14 | UDL-14 | 3004 | 2995 | 99.7 |
| Ex. 2-15 | UDL-15 | 2996 | 2982 | 99.5 |
| Ex. 2-16 | UDL-16 | 2990 | 2975 | 99.5 |
| Ex. 2-17 | UDL-17 | 3010 | 2984 | 99.1 |

TABLE 6-continued

| | Composition for forming organic film | Film thickness at 180° C.: A (Å) | Film thickness at 450° C.: B (Å) | (B/A) × 100 (%) |
|---|---|---|---|---|
| Ex. 2-18 | UDL-18 | 2988 | 2975 | 99.6 |
| Ex. 2-19 | UDL-19 | 3020 | 3002 | 99.4 |
| Ex. 2-20 | UDL-20 | 3018 | 3003 | 99.5 |
| Com. Ex. 2-1 | comparative UDL-1 | 3007 | 2277 | 75.7 |
| Com. Ex. 2-2 | comparative UDL-2 | 3011 | 2484 | 82.5 |
| Com. Ex. 2-3 | comparative UDL-3 | 3010 | 2118 | 70.4 |
| Com. Ex. 2-4 | comparative UDL-4 | 3015 | 2466 | 81.8 |
| Com. Ex. 2-5 | comparative UDL-5 | 3011 | 2203 | 73.2 |
| Com. Ex. 2-6 | comparative UDL-6 | 2985 | 2407 | 80.6 |
| Com. Ex. 2-7 | comparative UDL-7 | 2990 | 2168 | 72.5 |
| Com. Ex. 2-8 | comparative UDL-8 | 3003 | 2588 | 86.2 |
| Com. Ex. 2-9 | comparative UDL-9 | 2998 | 2229 | 74.3 |
| Com. Ex. 2-10 | comparative UDL-10 | 2985 | 2594 | 86.9 |
| Com. Ex. 2-11 | comparative UDL-11 | 2990 | 2162 | 72.3 |
| Com. Ex. 2-12 | comparative UDL-12 | 2992 | 2442 | 81.6 |
| Com. Ex. 2-13 | comparative UDL-13 | 3012 | 2217 | 73.6 |
| Com. Ex. 2-14 | comparative UDL-14 | 3000 | 2493 | 83.1 |
| Com. Ex. 2-15 | comparative UDL-1 | 3007 | 2340 | 77.8 |
| Com. Ex. 2-16 | comparative UDL-3 | 3010 | 2287 | 76.0 |
| Com. Ex. 2-17 | comparative UDL-5 | 3018 | 2379 | 78.8 |
| Com. Ex. 2-18 | comparative UDL-7 | 2980 | 2266 | 76.0 |
| Com. Ex. 2-19 | comparative UDL-9 | 2990 | 2235 | 74.7 |
| Com. Ex. 2-20 | comparative UDL-11 | 3009 | 2319 | 77.1 |

As shown in Table 6, in Examples 2-1 to 2-20 using the inventive compositions for forming an organic film, the film thicknesses were decreased by less than 1% even after the baking at 450° C. The inventive compositions for forming an organic film kept the film thicknesses even after the baking at 450° C. This indicates that the inventive compositions for forming an organic film have high heat resistance. In contrast, in Comparative Examples 2-1 to 2-14, the film thicknesses were decreased much more than those of the inventive compositions for forming an organic film. Even in Comparative Examples 2-2, 2-4, 2-6, 2-8, 2-10, 2-12, and 2-14 in which the crosslinking agent was added for curing, the film thicknesses were decreased by 10% or more. Further, in Comparative Examples 2-15 to 2-20 in which the baking was performed in the atmosphere at 450° C., since the baking was performed in the presence of oxygen, the thermal decomposition was facilitated by the oxidation, consequently decreasing the film thicknesses greatly. In Examples 2-1 to 2-20 using the inventive compositions for forming an organic film, the film thicknesses after the baking at 180° C. were retained after the baking under the nitrogen atmosphere at 450° C. This indicates that the inventive compositions for forming an organic film exhibit excellent heat resistance in an inert gas.

Example 3: Filling Property Evaluation (Examples 3-1 to 3-20, Comparative Examples 3-1 to 3-14)

Figure 3:
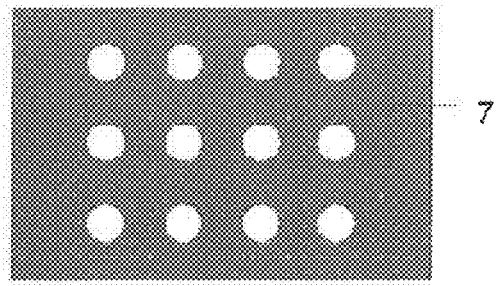
FIG. 3 is an explanatory view of a method for evaluating the filling property in Examples.
Figure 3:
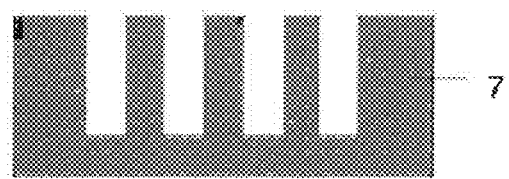
Figure 3:
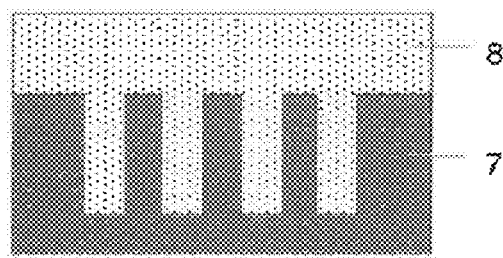

As shown in FIG. 3, the compositions (UDL-1 to -20, comparative UDL-1 to -14) for forming an organic film prepared above were each applied onto a SiO$_2$ wafer substrate having a dense hole pattern (hole diameter: 0.16 μm, hole depth: 0.50 μm, distance between the centers of adjacent two holes: 0.32 μm) and baked with a hot plate at 450° C. for 60 seconds under such a nitrogen stream that the oxygen concentration was controlled to 0.2% or less. Thereby, an organic film 8 was formed. The substrate used was a base substrate 7 (SiO$_2$ wafer substrate) having a dense hole pattern as shown in FIG. 3 (G) (top view) and (H) (sectional view). The sectional shapes of the resulting wafer substrates were observed with a scanning electron microscope (SEM) to check whether or not the holes were filled with the organic film without voids (space). Table 7 shows the result. If a composition for forming an organic film having poor filling property is used, voids occur inside the holes in this evaluation. If a composition for forming an organic film having good filling property is used, the holes are filled with the organic film without voids in this evaluation as shown in FIG. 3 (I).

TABLE 7

| | Composition for forming organic film | Presence/absence of voids |
|---|---|---|
| Ex. 3-1 | UDL-1 | absence |
| Ex. 3-2 | UDL-2 | absence |
| Ex. 3-3 | UDL-3 | absence |
| Ex. 3-4 | UDL-4 | absence |
| Ex. 3-5 | UDL-5 | absence |
| Ex. 3-6 | UDL-6 | absence |
| Ex. 3-7 | UDL-7 | absence |
| Ex- 3-8 | UDL-8 | absence |
| Ex. 3-9 | UDL-9 | absence |
| Ex. 3-10 | UDL-10 | absence |
| Ex. 3-11 | UDL-11 | absence |
| Ex. 3-12 | UDL-12 | absence |
| Ex. 3-13 | UDL-13 | absence |
| Ex. 3-14 | UDL-14 | absence |
| Ex. 3-15 | UDL-15 | absence |
| Ex. 3-16 | UDL-16 | absence |
| Ex. 3-17 | UDL-17 | absence |
| Ex. 3-18 | UDL-18 | absence |
| Ex. 3-19 | UDL-19 | absence |
| Ex. 3-20 | UDL-20 | absence |
| Com. Ex. 3-1 | comparative UDL-1 | presence |
| Com. Ex. 3-2 | comparative UDL-2 | presence |
| Com. Ex. 3-3 | comparative UDL-3 | presence |
| Com. Ex. 3-4 | comparative UDL-4 | presence |
| Com. Ex. 3-5 | comparative UDL-5 | presence |
| Com. Ex. 3-6 | comparative UDL-6 | presence |
| Com. Ex. 3-7 | comparative UDL-7 | presence |
| Com. Ex. 3-8 | comparative UDL-8 | presence |

TABLE 7-continued

| | Composition for forming organic film | Presence/absence of voids |
|---|---|---|
| Com. Ex. 3-9 | comparative UDL-9 | presence |
| Com. Ex. 3-10 | comparative UDL-10 | presence |
| Com. Ex. 3-11 | comparative UDL-11 | presence |
| Com. Ex. 3-12 | comparative UDL-12 | presence |
| Com. Ex. 3-13 | comparative UDL-13 | presence |
| Com. Ex. 3-14 | comparative UDL-14 | presence |

As shown in Table 7, Examples 3-1 to 3-20 using the inventive compositions for forming an organic film enabled the hole patterns to be filled without voids, confirming that the filling property was favorable. Meanwhile, in Comparative Examples 3-1 to 3-14, voids occurred, confirming that the filling property was poor. This result indicates that introducing the partial structure represented by Y in the general formula (1) provides flowability to the inventive composition for forming an organic film and improves the filling property.

Example 4: Planarizing Property Evaluation
(Examples 4-1 to 4-20, Comparative Examples 4-1 to 4-14)

Figure 4:
FIG. 4 is an explanatory view of a method for evaluating the planarizing property in Examples.
Figure 4:

The compositions (UDL-1 to -20, comparative UDL-1 to -14) for forming an organic film prepared above were each applied onto a base substrate 9 (SiO$_2$ wafer substrate) having a giant isolated trench pattern (FIG. 4 (J), trench width: 10 μm, trench depth: 0.50 μm), and baked at 450° C. for 60 seconds under such a nitrogen stream that the oxygen concentration was controlled to 0.2% or less. Then, a step (delta 10 in FIG. 4 (K)) between the trench portion and the non-trench portion of an organic film 10 was observed with an atomic force microscope (AFM) NX10 manufactured by Park systems Corp. Table 8 shows the result. In this evaluation, the smaller the step, the better the planarizing property. Note that, in this evaluation, a trench pattern having a depth of 0.10 μm was generally planarized using a composition for forming an organic film having a film thickness of approximately 0.2 μm. This is a special and severe evaluation condition to evaluate the planarizing property.

TABLE 8

| | Composition for forming organic film | Step (nm) |
|---|---|---|
| Ex. 4-1 | UDL-1 | 40 |
| Ex. 4-2 | UDL-2 | 35 |
| Ex. 4-3 | UDL-3 | 45 |
| Ex. 4-4 | UDL-4 | 40 |
| Ex. 4-5 | UDL-5 | 40 |
| Ex. 4-6 | UDL-6 | 45 |
| Ex. 4-7 | UDL-7 | 40 |
| Ex- 4-8 | UDL-8 | 40 |
| Ex. 4-9 | UDL-9 | 40 |
| Ex. 4-10 | UDL-10 | 35 |
| Ex. 4-11 | UDL-11 | 35 |
| Ex. 4-12 | UDL-12 | 30 |
| Ex. 4-13 | UDL-13 | 40 |
| Ex. 4-14 | UDL-14 | 40 |
| Ex. 4-15 | UDL-15 | 30 |
| Ex. 4-16 | UDL-16 | 35 |
| Ex. 4-17 | UDL-17 | 35 |
| Ex. 4-18 | UDL-18 | 35 |
| Ex. 4-19 | UDL-19 | 35 |
| Ex. 4-20 | UDL-20 | 30 |
| Com. Ex. 4-1 | comparative UDL-1 | 80 |
| Com. Ex. 4-2 | comparative UDL-2 | 90 |
| Com. Ex. 4-3 | comparative UDL-3 | 85 |
| Com. Ex. 4-4 | comparative UDL-4 | 95 |
| Com. Ex. 4-5 | comparative UDL-5 | 80 |
| Com. Ex. 4-6 | comparative UDL-6 | 90 |
| Com. Ex. 4-7 | comparative UDL-7 | 75 |
| Com. Ex. 4-8 | comparative UDL-8 | 90 |
| Com. Ex. 4-9 | comparative UDL-9 | 80 |
| Com. Ex. 4-10 | comparative UDL-10 | 90 |
| Com. Ex. 4-11 | comparative UDL-11 | 80 |
| Com. Ex. 4-12 | comparative UDL-12 | 95 |
| Com. Ex. 4-13 | comparative UDL-13 | 90 |
| Com. Ex. 4-14 | comparative UDL-14 | 95 |

As shown in Table 8, in Examples 4-1 to 4-20 using the inventive compositions for forming an organic film, the organic films had smaller steps between the trench portion and the non-trench portion than those in Comparative Examples 4-1 to 4-14, confirming that the planarizing property is more excellent. Particularly, among Comparative Examples, the cured films formed by adding the crosslinking agent and the thermal acid generator to the compositions for forming an organic film consequently had much worse planarizing property. From this result also, introducing the partial structure represented by Y in the general formula (1) of the present invention showed significant differences regarding planarizing property. Moreover, the comparison between Examples 4-17 to 4-20 using the compositions for forming an organic film to which the high-boiling-point solvent was added and Examples 4-6, 4-10 using the compositions for forming an organic film to which the high-boiling-point solvent was not added revealed that adding the high-boiling-point solvent further improves planarizing property.

Example 0.5: Patterning Test (Examples 5-1 to 5-20, Comparative Examples 5-1 to 5-14)

The compositions (UDL-1 to -20, comparative UDL-1 to -14) for forming an organic film prepared above were each applied onto a silicon wafer substrate on which a SiO$_2$ film of 300 nm had been formed. Then, the resulting substrate was baked at 450° C. for 60 seconds under such a nitrogen stream that the oxygen concentration was controlled to 0.2% or less. Thereby, an organic film (resist underlayer film) was formed. A CVD-SiON hard mask was formed thereon, and further an organic antireflective film composition (ARC-29A: manufactured by Nissan Chemical Industries, Ltd.) was applied and baked at 210° C. for 60 seconds to form an organic antireflective film having a film thickness of 80 nm. A monolayer resist for ArF was applied thereon as a resist upper layer film composition and baked at 105° C. for 60 seconds to form a photoresist film having a film thickness of 100 nm. A liquid immersion top coat composition (TC-1) was applied on the photoresist film and baked at 90° C. for 60 seconds to form a top coat having a film thickness of 50 nm.

The resist upper layer film composition (monolayer resist for ArF) was prepared by: dissolving a polymer (RP1), an acid generator (PAG1), and a basic compound (Amine1) into a solvent containing 0.1 mass % FC-430 (manufactured by Sumitomo 3M Ltd.) in proportions shown in Table 9; and filtering the solution through a 0.1-μm filter made of a fluorinated resin.

TABLE 9

| | Polymer (part by mass) | Acid generator (part by mass) | Basic compound (part by mass) | Solvent (part by mass) |
|---|---|---|---|---|
| Monolayer resist for ArF | RP1 (100) | PAG1 (6.6) | Amine1 (0.8) | PGMEA (2500) |

The polymer (RP1), acid generator (PAG1), and basic compound (Amine1) used are shown below.

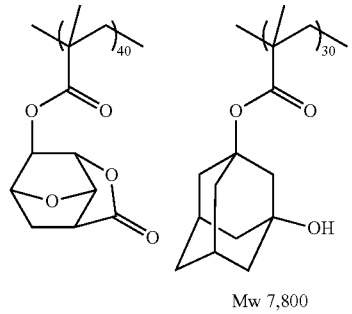

RP1

Mw 7,800

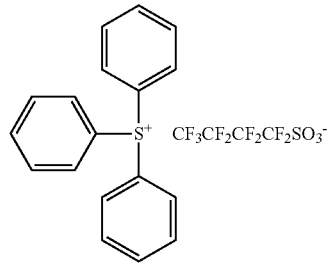

PAG1

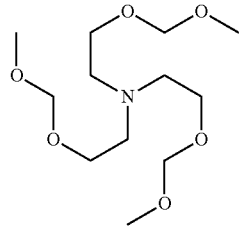

Amine1

The liquid immersion top coat composition (TC-1) was prepared by: dissolving a top coat polymer (PP1) into organic solvents in proportions shown in Table 10; and filtering the solution through a 0.1-μm filter made of a fluorinated resin.

TABLE 10

| | Polymer (part by mass) | Organic solvent (part by mass) |
|---|---|---|
| TC-1 | PP1 (100) | diisoamyl ether (2700) 2-methyl-1-butanol (270) |

The top coat polymer (PP1) used is shown below.

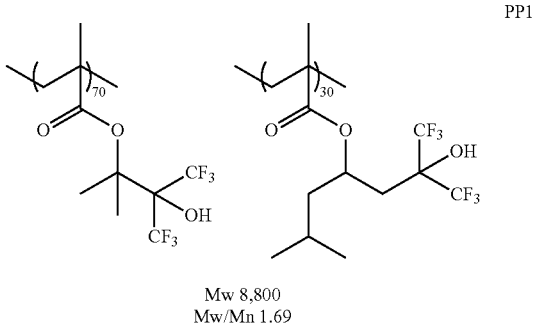

PP1

Mw 8,800
Mw/Mn 1.69

Next, the resulting substrate was exposed to light with an ArF liquid immersion exposure apparatus (NSR-S610C manufactured by Nikon Corporation, NA: 1.30, σ: 0.98/0.65, 35° s-polarized dipole illumination, 6% halftone phase shift mask), baked at 100° C. for 60 seconds (PEB), and developed with a 2.38 mass % tetramethylammonium hydroxide (TMAH) aqueous solution for 30 seconds. Thus, a 55 nm 1:1 positive line and space pattern was obtained.

Next, the organic antireflective film and the CVD-SiON hard mask were processed by dry etching using the resist pattern as a mask with an etching apparatus Telius manufactured by Tokyo Electron Limited to form a hard mask pattern. The organic film was etched using the obtained hard mask pattern as a mask to form an organic film pattern. The $SiO_2$ film was processed by etching using the obtained organic film pattern as a mask. The etching conditions were as described below.

Conditions for transferring the resist pattern to the SiON hard mask.
Chamber pressure: 10.0 Pa
RF power: 1,500 W
$CF_4$ gas flow rate: 75 sccm
$O_2$ gas flow rate: 15 sccm
Time: 15 sec Conditions for transferring the hard mask pattern to the organic film.
Chamber pressure: 2.0 Pa
RF power: 500 W
Ar gas flow rate: 75 sccm
O2 gas flow rate: 45 sccm
Time: 120 sec Conditions for transferring the organic film pattern to the $SiO_2$ film.
Chamber pressure: 2.0 Pa
RF power: 2,200 W
$C_5F_2$ gas flow rate: 20 sccm
$C_2F_6$ gas flow rate: 10 sccm
Ar gas flow rate: 300 sccm
$O_2$ gas flow rate: 60 sccm
Time: 90 sec The pattern cross sections were observed with an electron microscope (S-4700) manufactured by Hitachi, Ltd. Table 11 shows the result.

TABLE 11

|  | Composition for forming organic film | Pattern profile after etching for transferring to substrate |
|---|---|---|
| Ex. 5-1 | UDL-1 | vertical profile |
| Ex. 5-2 | UDL-2 | vertical profile |
| Ex. 5-3 | UDL-3 | vertical profile |
| Ex. 5-4 | UDL-4 | vertical profile |
| Ex. 5-5 | UDL-5 | vertical profile |
| Ex. 5-6 | UDL-6 | vertical profile |
| Ex. 5-7 | UDL-7 | vertical profile |
| Ex- 5-8 | UDL-8 | vertical profile |
| Ex. 5-9 | UDL-9 | vertical profile |
| Ex. 5-10 | UDL-10 | vertical profile |
| Ex. 5-11 | UDL-11 | vertical profile |
| Ex. 5-12 | UDL-12 | vertical profile |
| Ex. 5-13 | UDL-13 | vertical profile |
| Ex. 5-14 | UDL-14 | vertical profile |
| Ex. 5-15 | UDL-15 | vertical profile |
| Ex. 5-16 | UDL-16 | vertical profile |
| Ex. 5-17 | UDL-17 | vertical profile |
| Ex. 5-18 | UDL-18 | vertical profile |
| Ex. 5-19 | UDL-19 | vertical profile |
| Ex. 5-20 | UDL-20 | vertical profile |
| Com. Ex. 5-1 | comparative UDL-1 | pattern collapse |
| Com. Ex. 5-2 | comparative UDL-2 | vertical profile |
| Com. Ex. 5-3 | comparative UDL-3 | pattern collapse |
| Com. Ex. 5-4 | comparative UDL-4 | vertical profile |
| Com. Ex. 5-5 | comparative UDL-5 | pattern collapse |
| Com. Ex. 5-6 | comparative UDL-6 | vertical profile |
| Com. Ex. 5-7 | comparative UDL-7 | pattern collapse |
| Com. Ex. 5-8 | comparative UDL-8 | vertical profile |
| Com. Ex. 5-9 | comparative UDL-9 | pattern collapse |
| Com. Ex. 5-10 | comparative UDL-10 | vertical profile |
| Com. Ex. 5-11 | comparative UDL-11 | pattern collapse |
| Com. Ex. 5-12 | comparative UDL-12 | vertical profile |
| Com. Ex. 5-13 | comparative UDL-13 | pattern collapse |
| Com. Ex. 5-14 | comparative UDL-14 | vertical profile |

As shown in Table 11, as a result of any of Examples 5-1 to 5-20 using the inventive compositions for forming an organic film, the resist upper layer film pattern was favorably transferred to the final substrate, confirming that the inventive compositions for forming an organic film are suitably used in fine patterning according to the multilayer resist method. Meanwhile, in Comparative Examples 5-1, 5-3, 5-5, 5-7, 5-9, 5-11, and 5-13, the heat resistance under the nitrogen atmosphere was insufficient, and solvent resistance was not exhibited as described in Example 1. Hence, a cured film was not formed, pattern collapse occurred at patterning, and favorable patterns were not obtained in the end. In Comparative Examples 5-2, 5-4, 5-6, 5-8, 5-10, 5-12, and 5-14, the heat resistance was insufficient, but the patterns were formed.

Example 6: Patterning Test (Examples 6-1 to 6-20, Comparative Examples 6-1 to 6-14)

Coating films were formed by the same methods as those in Example 5, except that the compositions (UDL-1 to -20, comparative UDL-1 to -14) for forming an organic film prepared above were each applied onto a $SiO_2$ wafer substrate having a trench pattern (trench width: 10 μm, trench depth: 0.10 μm) and baked at 450° C. for 60 seconds under such a nitrogen stream that the oxygen concentration was controlled to 0.2% or less. Then, the coating films were subjected to patterning and dry etching, and the resulting pattern profiles were observed. Table 12 shows these results.

TABLE 12

|  | Composition for forming organic film | Pattern profile after etching for transferring to substrate |
|---|---|---|
| Ex. 6-1 | UDL-1 | vertical profile |
| Ex. 6-2 | UDL-2 | vertical profile |
| Ex. 6-3 | UDL-3 | vertical profile |
| Ex. 6-4 | UDL-4 | vertical profile |
| Ex. 6-5 | UDL-5 | vertical profile |
| Ex. 6-6 | UDL-6 | vertical profile |
| Ex. 6-7 | UDL-7 | vertical profile |
| Ex- 6-8 | UDL-8 | vertical profile |
| Ex. 6-9 | UDL-9 | vertical profile |
| Ex. 6-10 | UDL-10 | vertical profile |
| Ex. 6-11 | UDL-11 | vertical profile |
| Ex. 6-12 | UDL-12 | vertical profile |
| Ex. 6-13 | UDL-13 | vertical profile |
| Ex. 6-14 | UDL-14 | vertical profile |
| Ex. 6-15 | UDL-15 | vertical profile |
| Ex. 6-16 | UDL-16 | vertical profile |
| Ex. 6-17 | UDL-17 | vertical profile |
| Ex. 6-18 | UDL-18 | vertical profile |
| Ex. 6-19 | UDL-19 | vertical profile |
| Ex. 6-20 | UDL-20 | vertical profile |
| Com. Ex. 6-1 | comparative UDL-1 | pattern collapse |
| Com. Ex. 6-2 | comparative UDL-2 | pattern collapse |
| Com. Ex. 6-3 | comparative UDL-3 | pattern collapse |
| Com. Ex. 6-4 | comparative UDL-4 | pattern collapse |
| Com. Ex. 6-5 | comparative UDL-5 | pattern collapse |
| Com. Ex. 6-6 | comparative UDL-6 | pattern collapse |
| Com. Ex. 6-7 | comparative UDL-7 | pattern collapse |
| Com. Ex. 6-8 | comparative UDL-8 | pattern collapse |
| Com. Ex. 6-9 | comparative UDL-9 | pattern collapse |
| Com. Ex. 6-10 | comparative UDL-10 | pattern collapse |
| Com. Ex. 6-11 | comparative UDL-11 | pattern collapse |
| Com. Ex. 6-12 | comparative UDL-12 | pattern collapse |
| Com. Ex. 6-13 | comparative UDL-13 | pattern collapse |
| Com. Ex. 6-14 | comparative UDL-14 | pattern collapse |

As shown in Table 12, in any of Examples 6-1 to 6-20 using the inventive compositions for forming an organic film, the resist upper layer film pattern was favorably transferred to the final substrate, confirming that the inventive compositions for forming an organic film also have favorable filling property and are suitably used in fine patterning according to the multilayer resist method. Meanwhile, in Comparative Examples 6-1 to 6-14, even when solvent resistance was exhibited and a cured film was formed, the pattern was poorly filled. Hence, pattern collapse occurred at patterning, and favorable patterns were not obtained in the end.

From the above, it was revealed that the inventive compositions for forming an organic film containing the inventive polymer have favorable dry etching resistance and also have heat resistance to 400° C. or higher and high filling and planarizing properties even in an oxygen-free inert gas. Thus, the inventive compositions for forming an organic film are quite useful as compositions for forming an organic film used in multilayer resist methods. Moreover, the inventive patterning processes using these compositions can precisely form a fine pattern even when a body to be processed is a stepped substrate.

It should be noted that the present invention is not restricted to the above-described embodiments. The embodiments are merely examples so that any embodiments that have substantially the same feature and demonstrate the same functions and effects as those in the technical concept as disclosed in claims of the present invention are included in the technical range of the present invention.

What is claimed is:

1. A composition for forming an organic film, comprising:
(A) a polymer having a repeating unit shown by the following general formula (1); and
(B) an organic solvent,

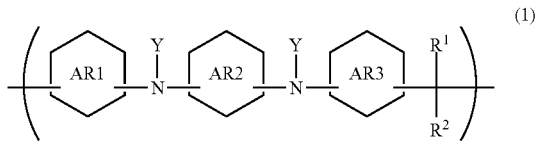

(1)

wherein AR1, AR2, and AR3 each represent a benzene ring, a naphthalene ring, or an anthracene ring which optionally have a substituent; carbon atoms on aromatic rings of AR1 and AR2, or AR2 and AR3, optionally bond to each other directly or via a linking group to form a bridge structure; $R^1$ and $R^2$ each independently represent a hydrogen atom or an organic group having 1 to 30 carbon atoms; when $R^1$ and $R^2$ are the organic groups, $R^1$ and $R^2$ optionally bond to each other within a molecule to form a cyclic organic group; and Y represents a group shown by the following formula (2), $$-R^3-C\equiv C-R^4 \quad (2)$$

wherein $R^3$ represents a single bond or a divalent organic group having 1 to 20 carbon atoms; $R^4$ represents a hydrogen atom or a monovalent organic group having 1 to 20 carbon atoms; and a dotted line represents a bonding arm.

2. The composition for forming an organic film according to claim 1, wherein the component (A) has a weight average molecular weight of 500 to 20,000.

3. The composition for forming an organic film according to claim 1, further comprising at least one of (C) an acid generator, (D) a surfactant, (E) a crosslinking agent, and (F) a plasticizer.

4. The composition for forming an organic film according to claim 2, further comprising at least one of (C) an acid generator, (D) a surfactant, (E) a crosslinking agent, and (F) a plasticizer.

5. A substrate for manufacturing a semiconductor apparatus, comprising an organic film on the substrate, the organic film being formed by curing the composition for forming an organic film according to claim 1.

6. A method for forming an organic film employed in a semiconductor apparatus manufacturing process, the method comprising:
spin-coating a body to be processed with the composition for forming an organic film according to claim 1; and
heating the body to be processed coated with the composition for forming an organic film under an inert gas atmosphere at a temperature of 50° C. or higher to 600° C. or lower within a range of 5 seconds to 7200 seconds to obtain a cured film.

7. A method for forming an organic film employed in a semiconductor apparatus manufacturing process, the method comprising:
spin-coating a body to be processed with the composition for forming an organic film according to claim 1;
heating the body to be processed coated with the composition for forming an organic film in air at a temperature of 50° C. or higher to 300° C. or lower within a range of 5 seconds to 600 seconds to form a coating film; and
then heating the body to be processed having the formed coating film under an inert gas atmosphere at a temperature of 200° C. or higher to 600° C. or lower within a range of 10 seconds to 7200 seconds to obtain a cured film.

8. The method for forming an organic film according to claim 6, wherein the inert gas has an oxygen concentration of 1% or less.

9. The method for forming an organic film according to claim 6, wherein the body to be processed has a structure or a step with a height of 30 nm or more.

10. A patterning process comprising:
forming an organic film on a body to be processed from the composition for forming an organic film according to claim 1;
forming a silicon-containing resist middle layer film on the organic film from a silicon-containing resist middle layer film composition;
forming a resist upper layer film on the silicon-containing resist middle layer film from a resist upper layer film composition composed of a photoresist composition;
forming a circuit pattern in the resist upper layer film;
transferring the pattern to the silicon-containing resist middle layer film by etching using the resist upper layer film having the formed circuit pattern as a mask;
transferring the pattern to the organic film by etching using the silicon-containing resist middle layer film having the transferred pattern as a mask; and
further transferring the pattern to the body to be processed by etching using the organic film having the transferred pattern as a mask.

11. A patterning process comprising:
forming an organic film on a body to be processed from the composition for forming an organic film according to claim 1;
forming a silicon-containing resist middle layer film on the organic film from a silicon-containing resist middle layer film composition;
forming an organic antireflective film on the silicon-containing resist middle layer film;
forming a resist upper layer film on the organic antireflective film from a resist upper layer film composition composed of a photoresist composition, so that a 4-layered film structure is constructed;
forming a circuit pattern in the resist upper layer film;
transferring the pattern to the organic antireflective film and the silicon-containing resist middle layer film by etching using the resist upper layer film having the formed circuit pattern as a mask;
transferring the pattern to the organic film by etching using the silicon-containing resist middle layer film having the transferred pattern as a mask; and
further transferring the pattern to the body to be processed by etching using the organic film having the transferred pattern as a mask.

12. A patterning process comprising:
forming an organic film on a body to be processed from the composition for forming an organic film according to claim 1;
forming an inorganic hard mask selected from a silicon oxide film, a silicon nitride film, a silicon oxynitride film, a titanium oxide film, and a titanium nitride film on the organic film;

forming a resist upper layer film on the inorganic hard mask from a resist upper layer film composition composed of a photoresist composition;

forming a circuit pattern in the resist upper layer film;

transferring the pattern to the inorganic hard mask by etching using the resist upper layer film having the formed circuit pattern as a mask;

transferring the pattern to the organic film by etching using the inorganic hard mask having the formed pattern as a mask; and further transferring the pattern to the body to be processed by etching using the organic film having the formed pattern as a mask.

13. A patterning process comprising:

forming an organic film on a body to be processed from the composition for forming an organic film according to claim 1;

forming an inorganic hard mask selected from a silicon oxide film, a silicon nitride film, a silicon oxynitride film, a titanium oxide film, and a titanium nitride film on the organic film;

forming an organic antireflective film on the inorganic hard mask;

forming a resist upper layer film on the organic antireflective film from a resist upper layer film composition composed of a photoresist composition, so that a 4-layered film structure is constructed;

forming a circuit pattern in the resist upper layer film;

transferring the pattern to the organic antireflective film and the inorganic hard mask by etching using the resist upper layer film having the formed circuit pattern as a mask;

transferring the pattern to the organic film by etching using the inorganic hard mask having the formed pattern as a mask; and further transferring the pattern to the body to be processed by etching using the organic film having the formed pattern as a mask.

14. The patterning process according to claim 12, wherein the inorganic hard mask is formed by a CVD method or an ALD method.

15. The patterning process according to claim 13, wherein the inorganic hard mask is formed by a CVD method or an ALD method.

16. The patterning process according to claim 10, wherein the circuit pattern is formed by a lithography using light with a wavelength ranging from 10 nm to 300 nm, a direct drawing by electron beam, a nanoimprinting, or a combination thereof.

17. The patterning process according to claim 10, wherein when the circuit pattern is formed, the circuit pattern is developed by alkaline development or development with an organic solvent.

18. The patterning process according to claim 10, wherein the body to be processed is a semiconductor apparatus substrate or the semiconductor apparatus substrate coated with any of a metal film, a metal carbide film, a metal oxide film, a metal nitride film, a metal oxycarbide film, and a metal oxynitride film.

19. The patterning process according to claim 18, wherein the metal of the body to be processed is silicon, titanium, tungsten, hafnium, zirconium, chromium, germanium, copper, silver, gold, aluminum, indium, gallium, arsenic, palladium, iron, tantalum, iridium, molybdenum, or an alloy thereof.

20. A polymer comprising a repeating unit shown by the following general formula (1),

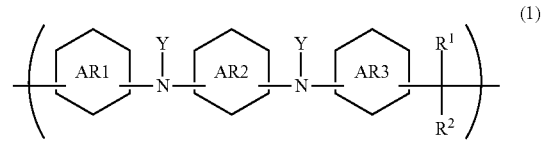

(1)

wherein AR1, AR2, and AR3 each represent a benzene ring, a naphthalene ring, or an anthracene ring which optionally have a substituent; carbon atoms on aromatic rings of AR1 and AR2, or AR2 and AR3, optionally bond to each other directly or via a linking group to form a bridge structure; $R^1$ and $R^2$ each independently represent a hydrogen atom or an organic group having 1 to 30 carbon atoms; when $R^1$ and $R^2$ are the organic groups, $R^1$ and $R^2$ optionally bond to each other within a molecule to form a cyclic organic group; and Y represents a group shown by the following formula (2),

$-R^3-C\equiv C-R^4$ (2)

wherein $R^3$ represents a single bond or a divalent organic group having 1 to 20 carbon atoms; $R^4$ represents a hydrogen atom or a monovalent organic group having 1 to 20 carbon atoms; and a dotted line represents a bonding arm.

* * * * *